(12) United States Patent
Francis et al.

(10) Patent No.: US 10,653,817 B2
(45) Date of Patent: May 19, 2020

(54) METHOD FOR PRODUCING AN IMPLANTABLE LIGAMENT AND TENDON REPAIR DEVICE

(71) Applicant: EMBODY INC., Norfolk, VA (US)

(72) Inventors: Michael P. Francis, Norfolk, VA (US); Yas Maghdouri-White, Norfolk, VA (US); Hilary Wriggers, Norfolk, VA (US); Nardos Sori, Norfolk, VA (US); Stella Petrova, Norfolk, VA (US); Seth Polk, Norfolk, VA (US); Nicholas Thayer, Norfolk, VA (US)

(73) Assignee: EMBODY INC., Norfolk, VA (US)

( * ) Notice: Subject to any disclaimer, the term of this patent is extended or adjusted under 35 U.S.C. 154(b) by 0 days.

(21) Appl. No.: 16/222,350

(22) Filed: Dec. 17, 2018

(65) Prior Publication Data

US 2019/0134267 A1 May 9, 2019

Related U.S. Application Data

(63) Continuation of application No. PCT/US2018/057412, filed on Oct. 24, 2018.
(Continued)

(51) Int. Cl.
*D01D 1/02* (2006.01)
*D01D 5/04* (2006.01)
(Continued)

(52) U.S. Cl.
CPC ........... *A61L 27/3662* (2013.01); *A61L 27/24* (2013.01); *A61L 27/26* (2013.01); *A61L 27/3804* (2013.01); *A61L 27/3834* (2013.01); *D01D 5/003* (2013.01); *D01D 5/0038* (2013.01); *D01D 5/0076* (2013.01); *A61L 2430/10* (2013.01)

(58) Field of Classification Search
CPC ........ D01D 1/02; D01D 5/003; D01D 5/0038; D01D 5/0076; D01D 5/04; D01D 7/00; D01D 10/02; D01F 4/00; D01F 4/02
USPC .... 264/10, 101, 204, 205, 211.12, 464, 465, 264/466, 484, 555, 235
See application file for complete search history.

(56) References Cited

U.S. PATENT DOCUMENTS 5,171,273 A 12/1992 Silver et al.
7,862,831 B2 1/2011 Wang et al.
(Continued)

FOREIGN PATENT DOCUMENTS

CN 1596996 A 3/2005
CN 107261210 A 10/2017
(Continued)

OTHER PUBLICATIONS

Liao et al., "In Vitro and in Vivo Degradation of Mineralized Collagen-Based Composite Scaffold: Nanohydroxyapatite/Collagen/Poly(L-lactide)", Tissue Engineering Part A, vol. 10, Issue 1-2, 2004, pp. 73-80.
(Continued)

*Primary Examiner* — Leo B Tentoni
(74) *Attorney, Agent, or Firm* — J. A. Lindeman & Co. PLLC; Jeffrey Lindeman

(57) ABSTRACT

Compositions and blends of biopolymers and bio-acceptable polymers are described, along with the use of benign solvent systems to prepare biocompatible scaffolds and surgically implantable devices for use in supporting and facilitating the repair of soft tissue injuries.

29 Claims, 17 Drawing Sheets
(16 of 17 Drawing Sheet(s) Filed in Color)

Related U.S. Application Data

(60) Provisional application No. 62/707,159, filed on Oct. 24, 2017, provisional application No. 62/714,367, filed on Aug. 3, 2018, provisional application No. 62/718,694, filed on Aug. 14, 2018.

(51) Int. Cl.
| | | |
|---|---|---|
| *D01D 7/00* | (2006.01) | |
| *D01D 10/02* | (2006.01) | |
| *D01F 4/00* | (2006.01) | |
| *D01F 4/02* | (2006.01) | |
| *A61L 27/36* | (2006.01) | |
| *A61L 27/38* | (2006.01) | |
| *A61L 27/26* | (2006.01) | |
| *D01D 5/00* | (2006.01) | |
| *A61L 27/24* | (2006.01) | |

(56) References Cited

U.S. PATENT DOCUMENTS

| | | |
|---|---|---|
| 7,878,786 B2 | 2/2011 | Yost et al. |
| 8,048,361 B2 | 11/2011 | Wang et al. |
| 8,318,903 B2 | 11/2012 | Dong et al. |
| 8,491,457 B2 | 7/2013 | Atala et al. |
| 8,585,753 B2 | 11/2013 | Scanlon et al. |
| 8,586,345 B2 | 11/2013 | Simpson et al. |
| 9,034,239 B2 | 5/2015 | Yun et al. |
| 9,198,750 B2 | 12/2015 | Van Kampen et al. |
| 9,393,104 B2 | 7/2016 | Kampen et al. |
| 9,421,305 B2 | 8/2016 | Lee et al. |
| 9,597,430 B2 | 3/2017 | Ratcliffe et al. |
| 9,683,011 B2 | 6/2017 | Wnek et al. |
| 9,757,132 B2 | 9/2017 | Laurencin et al. |
| 2002/0090725 A1 | 7/2002 | Simpson et al. |
| 2002/0100725 A1 | 8/2002 | Lee et al. |
| 2003/0105528 A1 | 6/2003 | Shimp et al. |
| 2003/0114937 A1 | 6/2003 | Leatherbury et al. |
| 2005/0008675 A1 | 1/2005 | Bhatia et al. |
| 2005/0113938 A1 | 5/2005 | Jamiolkowski et al. |
| 2006/0154063 A1 | 7/2006 | Fujihara et al. |
| 2006/0204539 A1 | 9/2006 | Atala et al. |
| 2007/0269481 A1 | 11/2007 | Li et al. |
| 2008/0051888 A1 | 2/2008 | Ratcliffe et al. |
| 2008/0188936 A1 | 8/2008 | Ball et al. |
| 2009/0240342 A1 | 9/2009 | Lindh, Sr. et al. |
| 2010/0063599 A1 | 3/2010 | Brunelle et al. |
| 2010/0145367 A1 | 6/2010 | Ratcliffe |
| 2010/0191332 A1 | 7/2010 | Euteneuer et al. |
| 2010/0291058 A1 | 11/2010 | Bowlin et al. |
| 2010/0292791 A1 | 11/2010 | Lu et al. |
| 2010/0331980 A1 | 12/2010 | Lee et al. |
| 2011/0238178 A1 | 9/2011 | Downes et al. |
| 2011/0293685 A1 | 12/2011 | Kuo et al. |
| 2012/0273993 A1 | 11/2012 | Shoseyov et al. |
| 2013/0095167 A1 | 4/2013 | Warnke |
| 2013/0149532 A1 | 6/2013 | Yun et al. |
| 2014/0011416 A1 | 1/2014 | Yang et al. |
| 2014/0051169 A1 | 2/2014 | Ganey et al. |
| 2015/0045454 A1 | 2/2015 | Kong et al. |
| 2015/0086607 A1 | 3/2015 | Johnson et al. |
| 2015/0230918 A1 | 8/2015 | Detamore et al. |
| 2015/0367030 A1 | 12/2015 | Murray |
| 2016/0015852 A1 | 1/2016 | Liou et al. |
| 2016/0068654 A1 | 3/2016 | Huh et al. |
| 2016/0106548 A1 | 4/2016 | Li et al. |
| 2016/0130558 A1 | 5/2016 | Baer |
| 2016/0136895 A1 | 5/2016 | Beyer et al. |
| 2016/0263280 A1 | 9/2016 | Harrell |
| 2016/0287374 A1 | 10/2016 | Soletti et al. |
| 2016/0296627 A1 | 10/2016 | Garcia et al. |
| 2016/0317281 A1 | 11/2016 | Van Kampen et al. |
| 2016/0325013 A1 | 11/2016 | Li et al. |
| 2016/0325022 A1 | 11/2016 | Liu et al. |
| 2017/0233834 A1 | 8/2017 | Purcell et al. |
| 2017/0273775 A1 | 9/2017 | Rocco et al. |
| 2018/0193524 A1 | 7/2018 | Shoseyov et al. |
| 2018/0368982 A1 | 12/2018 | Ball |

FOREIGN PATENT DOCUMENTS

| | | |
|---|---|---|
| EP | 2322234 B1 | 9/2005 |
| EP | 1216296 B1 | 4/2009 |
| EP | 1863547 B1 | 5/2016 |
| IN | 640CHE2013 A | 3/2013 |
| WO | 98/30252 A1 | 7/1998 |
| WO | 99/39724 A1 | 8/1999 |
| WO | 2007109304 A2 | 9/2007 |
| WO | 2008131293 A2 | 10/2008 |
| WO | 2009079211 A1 | 6/2009 |
| WO | 2009/149181 A2 | 12/2009 |
| WO | 2013/093921 A1 | 6/2013 |
| WO | 2013123147 A1 | 8/2013 |
| WO | 2013/172788 A1 | 11/2013 |
| WO | 2015/138970 A1 | 9/2015 |
| WO | 2016/042211 A1 | 3/2016 |
| WO | 2017053757 A1 | 3/2017 |
| WO | 2018092098 A1 | 5/2018 |
| WO | 2018212792 A2 | 11/2018 |

OTHER PUBLICATIONS

Cui et al., "Investigation of Drug Release and Matrix Degradation of Electrospun Poly(DL-lactide) Fibers with Paracetanol Inoculation", Biomacromolecules, 2006, 7, pp. 1623-1629.

D. Garlotta "A Literature Review of Poly(Lactic Acid)", Journal of Polymers and the Environment, vol. 9, No. 2, 2001, pp. 63-84.

Haider et al., "A comprehensive review summarizing the effect of electrospinning parameters and potential applications of nanofibers in biomedical and biotechnology", Arabian Journal of Chemistry, 2015, pp. 1-24.

Jamshidi et al., "Thermal characterization of polylactides", Polymer, 1988, vol. 29, pp. 2229-2234.

Katsogiannis et al., "Porous electrospun polycarprolactone (PCL) fibres by phase separation", European Polymer Journal, 2015, 69, pp. 284-295.

Li et al., "Recent advances in stereocomplexation of enantiomeric PLA-based copolymers and applications", Progress in Polymer Science, 2016, 62, pp. 22-72.

D. Lubasova and L. Martinova "Controlled Morphology of Porous Polyvinyl Butyral Nanofibers", Hindawi Publishing Corporation Journal of Nanomaterials, vol. 2011, Article ID 292516, 6 pages.

H. Tsuji "Poly(lactide) Stereocomplexes: Formation, Structure, Properties, Degradation, and Applications", Macroomol. Biosci., 2005, 5, pp. 569-597.

International Search Report and Written Opinion in International Application No. PCT/US2018/057412, dated Feb. 27, 2019.

"4 Figures: Liquid Crystalline Ordered Collagen Substrates for Applications in Tissue Engineering", ACS Biomaterials Science and Engineering, Mar. 2016, https://www.researchgate.net/publication/297595398.

Bishop et al., "Design of an Extrusion System to Optimize the Production of Self-Assembled Collagen Microthreads", Degree of Bachelor of Science Paper, Worcester Polytechnic Institute, Project No. GXP-0508. (Undated).

Dong et al., "Electrospinning of Collagen Nanofiber Scaffolds from Benign Solvents", Macromol. Rapid Commun. 2009, 30 pp. 539-542.

Gentleman et al., "Mechanical characterization of collagen fibers and scaffolds for tissue engineering", Biomaterials 2003, 24, pp. 3805-3813.

Hwang et al., "Effects of Zero-Length and Non-Zero-Length Cross-Linking Reagents on the Optical Spectral Properties and Structures of Collagen Hydrogels", ACS Appl. Mater. Interfaces., 2012, 4, pp. 261-267.

Liu et al., "Novel 3D collagen scaffolds fabricated by indirect printing technique for tissue engineering", Abstract, J. Biomedical Materials Research Part B: Applied Biomaterials, 2008, Issue 2; pp. 519-528.

(56) References Cited

OTHER PUBLICATIONS

Oryan et al., "Chemical crosslinking of biopolymeric scaffolds: Current knowledge and future directions of crosslinked engineered bone scaffolds", International Journal of Biological Macromolecules 2018, 107, pp. 678-688.
Punnoose et al., "Electrospun Type 1 Collagen matrices using a novel benign solvent for Cardiac tissue engineering", Journal of Cellular Physiology, 2015.
Salgado et al., "Bone Tissue Engineering: State of the Art and Future Trends", Abstract, Macromolecular Bioscience, 2004, vol. 4, Issue 8, pp. 743-765.
Synthasome X-Repair Technology, FAQs, http://www.synthasome.com/xRepair-technology.php; accessed Mar. 22, 2017.
Tutak et al., "The support of bone marrow stromal cell differentiation by airbrushed nanofibers scaffolds", Abstract, Biomaterials, 2013, vol. 34, Issue 10, pp. 2389-2398.
Wortmann et al., "New Polymers for Needlesless Electrospinning from Low-Toxic Solvents", Nanomaterials, 2019, 9, 52, pp. 1-11.
Wright Achilles Tendon Information, http://www.wright.com/healthcare-professionals/graftjacket/applications/achilles-tendon; accessed Nov. 12, 2017.
Zobitz et al., "Determination of the Compressive Material Properties of the Supraspinatus Tendon", Journal of Biomechanical Engineering, 2001, vol. 123, pp. 47-51.
Cheng et al., "Isolation, Characterization and Evaluation of Collagen from Jellyfish *Rhopilema esculentum* Kishinouye for Use in Hemostatic Applications", PLoS One 12(1), Jan. 19, 2017, pp. 1-21.
Hochleitner et al., "Melt electrowriting below the critical translation speed to fabricate crimped elastomer scaffolds with non-linear extension behaviour mimicking that of ligaments and tendons", Acta Biomaterialia 72 (2018), pp. 110-120.
Hochleitner et al., "Melt Electrowriting of Thermoplastic Elastomers", Macromolecular Rapid Communications, 2018, 39, 1800055, pp. 1-7.
Hoque et al., "Extrusion Based Rapid Prototyping Technique: An Advanced Platform for Tissue Engineering Scaffold Fabrication", Aug. 9, 2011, Biopolymers vol. 97, No. 2, pp. 83-93.
Hrynevich et al., "Dimension-Based Design of Melt Electrowritten Scaffolds", Nano-Micro Small, 2018, 14, 1800232, pp. 1-6.
Huang et al., "A review on polymer nanofibers by electrospinning and their applications in nanocomposites", composites Science and Technology 63 (2003), pp. 2223-2253.
Jha et al., "Electrospun Collagen: A Tissue Engineering Scaffold with Unique Functional Properties in aWide Variety of Applications", Journal of Nanomaterials, vol. 2011, Article ID 348268, pp. 1-15.
Krishnamoorthi et al., "Isolation and partial characterization of collagen from outer skin of Sepia pharaonis (Ehrenberg, 1831) from Puducherry coast", Biochemistry and Biophysics Reports 10 (2017) pp. 39-45.
Li et al., "3D-Printed Biopolymers for Tissue Engineering Application", International Journal of Polymer Science vol. 2014, Article ID 829145, pp. 1-13.
Lin et al., "Functionalized Poly(D,L-lactide) for Pulmonary Epithelial Cell Culture", Advanced Engineering Materials, Mar. 8, 2010 (Abstract).
Lu et al., "Techniques for fabrication and construction of three-dimensional scaffolds for tissue engineering", International Journal of Nanomedicine, Jan. 17, 2013, vol. 8, pp. 337-350.
Ma, "Scaffolds for tissue fabrication", Materialstoday, May 2004, pp. 30-40.
Addad et al., "Isolation, Characterization and Biological Evaluation of Jellyfish Collagen for Use in Biomedical Applications", Marine Drugs, Jun. 7, 2011, vol. 9, pp. 967-983.
Middleton et al., "Synthetic biodegradable polymers as orthopedic devices", Biomaterials 21 (2000) pp. 2335-2346.
Qiao e tal., "Compositional and in Vitro Evaluation of Nonwoven Type I Collagen/Poly-dl-lactic Acid Scaffolds for Bone Regeneration", Journal of Functional Biomaterials, 2015, vol. 6, pp. 667-686.
Rudolph et al., "Surface Modification of Biodegradable Polymers towards Better Biocompatibility and Lower Thrombogenicity", PLOS One, Dec. 7, 2015, pp. 1-17.
Sensini et al., "Biofabrication of bundles of poly(lactic acid)-collagen blends mimicking the fascicles of the human Achille tendon", IOP Publishing, Biofabrication, vol. 9 (2017) 015025.
Siow et al., "Plasma Methods for the Generation of Chemically Reactive Surfaces for Biomolecule Immobilization and Cell Colonization—A Review", Plasma Processes and Polymers, Jun. 2006, vol. 3, pp. 392-418.
Yang et al., "Tendon and Ligament Regeneration and Repair: Clinical Relevance and Developmental Paradigm", Birth Defects Res C Embryo Today, Sep. 2013, vol. 99(3). pp. 203-222.
Tham et al., "Surface Modification of Poly (lactic acid) (PLA) via Alkaline Hydrolysis Degradation", Advanced Materials Research, 2014, vol. 970, pp. 324-327. 4p. (Abstract).
Zagho et al., "Recent Trends in Electrospinning of Polymer Nanofibers and their Applications as Templates for Metal Oxide Nanofibers Preparation", INTECH open science, open minds, 2016, pp. 4-24.
Zhang et al., "Electrospun scaffolds from silk fibroin and their cellular compatibility", Journal of Biomedical Materials Research Part A, 2009, pp. 997-983.
Zhong et al., "Isolation and Characterization of Collagen from the Body Wall of Sea Cucumber *Stichopus monotuberculatus*", Journal of Food Science, vol. 80, No. 4, 2015, pp. 671-679.
Delguerra et al., "Optimization if the interaction between ethylene-vinyl alcohol copolymers and human endothelial cells", Journal of Materials Science: Materials in Medicine 7, 1996, 8-12.
Gabler et al., "In Vivo Evaluation of Different Collagen Scaffolds in an Achilles Tendon Defect Model", BioMed Research International, vol. 2018, Article ID 6432742, pp. 1-11.
Van Kampen et al., "Tissue-engineered augmentation of a rotator cuff tendon using a reconstituted collagen scaffold: a histological evaluation in sheep", Muscles, Ligaments and Tendons Journal, 2013, 3(3): pp. 229-235.
Elamparithi et al., "Electrospun type 1 collagen matrices preserving native ultrastructure using benign binary solvent for cardiac tissue engineering", Artificial Cells, Nanomedicine, and Biotechnology 2016, 44: 1318-1325.
Elamparithi et al., "Gelatin electrospun nanofibrous matrices for cardiac tissue engineering applications", International Journal of Polymeric Materials and Polymeric Biomaterials, 2017, vol. 66, No. 1, pp. 20-27.

FIG. 1A: Partially torn tendon

FIG. 1B: Suture repair

FIG. 1C: Implant wrapped around repair

FIG. 1D: Implant sutured in place

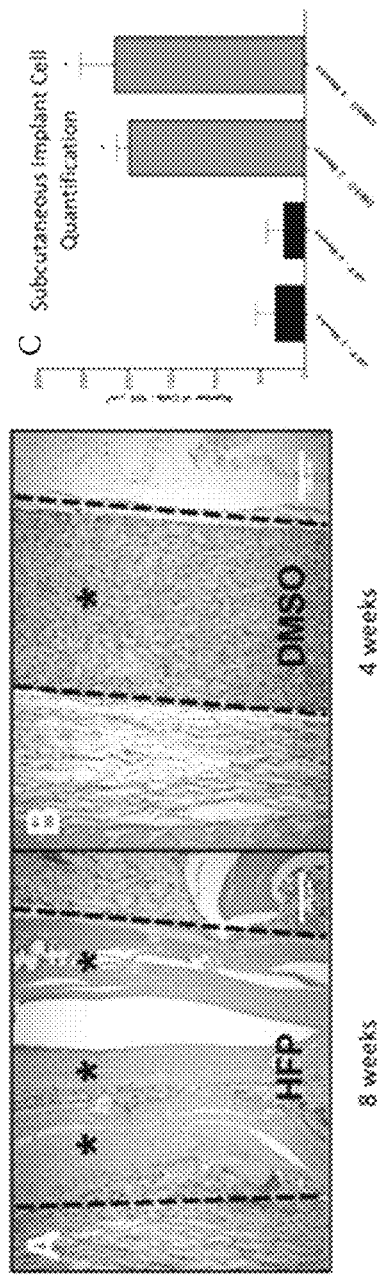
FIG. 6
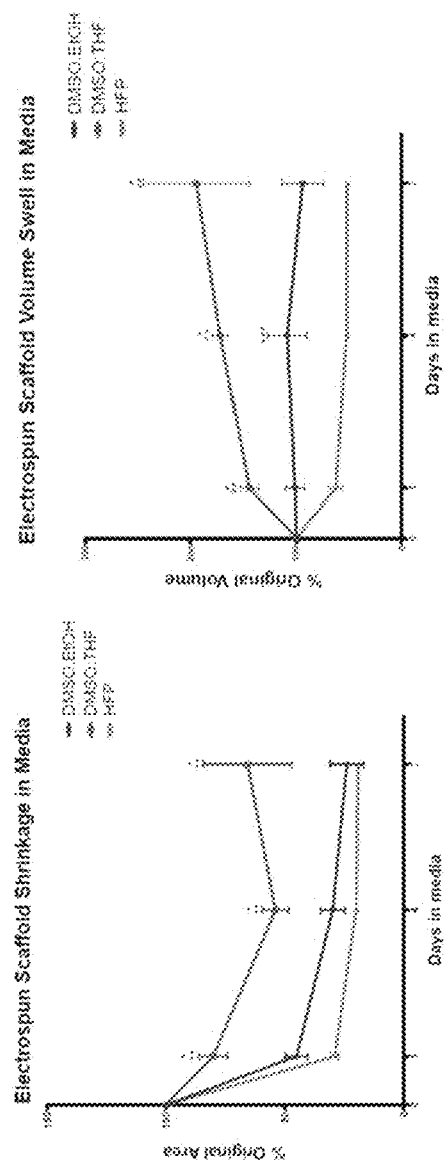
FIG. 7A
FIG. 7B
FIG. 7

METHOD FOR PRODUCING AN IMPLANTABLE LIGAMENT AND TENDON REPAIR DEVICE

CROSS-REFERENCE TO RELATED APPLICATIONS

This application is a Continuation Application of PCT International Application No. PCT/US2018/057412, filed Oct. 24, 2018; which is related to U.S. Provisional Patent Application Nos. 62/707,159, filed Oct. 24, 2017, 62/714,367, filed Aug. 3, 2018, and 62/718,694, filed Aug. 14, 2018, the content of which is hereby incorporated by reference in its entirety.

STATEMENT OF US GOVERNMENT SUPPORT

This invention was made with government support under DARPA Contract HR0011-15-9-0006. The US government has certain rights in the invention.

FIELD OF THE INVENTION

The invention relates to biopolymer scaffolds and implants for the management, protection and repair of injuries to soft tissue injuries such ligaments and tendons. The implants have improved physicochemical and biological properties including enhanced biocompatibility. The invention also relates to processes for the production of such implants using benign solvent systems.

BACKGROUND

Surgical repairs number around 800,000 annually in the US alone for ligaments and tendons of the foot and ankle (for example, Achilles tendon), shoulder (for example, rotator cuff), and knee (for example, anterior cruciate ligament), yet the current standards of care involving the implantation of replacement and supporting elements are generally considered by medical practitioners to be less than optimal.

Leading ligament and tendon repair graft products intended to provide biocompatible soft tissue support scaffolds often involve two decades old technologies that in some instance rely on cadaveric tissue or invasive autografting. Allografts are supply-limited, promote scar formation, may provoke an immune response, and have poorly defined turnover rates, all of which inhibit healing. Autografting also extends surgery time and associated trauma, and often adds a second costly procedure to recover the autologous tissue.

For example, the GRAFTJACKET® Regenerative Tissue Matrix is a sheet-like product formed from donated allograft human dermis, aseptically processed to remove cells and then freeze-dried, http://www.wright.com/footandankleproducts/graftjacket. ArthroFLEX® Decellularized Dermal Allograft is a similar acellular dermal extracellular matrix, https://www.arthrex.com/orthobiologics/arthroflex.

Various other approaches have been taken to develop synthetic or semi-synthetic components for implantable devices useful as scaffolds to facilitate repair of, or to support or replace damaged soft tissues such as tendons and ligaments. Such products must function in a variety of challenging biomechanical environments in which multiple functional parameters must be addressed, among them, for example, are compatibility, strength, flexibility and biodegradability.

Among such approaches and products are those disclosed, for example, by Ratcliffe et al., U.S. Pat. No. 9,597,430 (2017), entitled "Synthetic Structure for Soft Tissue Repair". This patent describes various synthetic fibrillar structures, such as a woven mesh and single or multilayer planar fibrillar forms. According to Ratcliffe, these structures can be made from any biocompatible polymer material capable of providing suitable mechanical properties, bioabsorbable or not. Collagen and lactide are mentioned as suitable. Synthasome's "X-Repair" medical device appears to be related to this patent and has been granted FDA 510(k) clearance by the US Food and Drug Administration (FDA), (http://www.synthasome.com/xRepair.php).

Another approach is described by Qiao et al., "Compositional and in Vitro Evaluation of Nonwoven Type I Collagen/Poly-dl-lactic Acid Scaffolds for Bone Regeneration," Journal of Functional Biomaterials 2015, 6, 667-686; doi: 10.3390/jfb6030667. This article describes electrospun blends of Poly-d,l-lactic acid (PDLLA) with type I collagen. Various blends are described with ratios of 40/60, 60/40 and 80/20 polymer blend by weight (PDLLA/Collagen). Qiao described a co-solvent system, and reported that chemical cross linking was essential to ensure long term stability of this material in cell culture. According to Qiao, scaffolds of PDLLA/collagen at a 60:40 weight ratio provided the greatest stability over a five-week culture period.

The use of constructs for muscle implants is also described by Lee et al., U.S. Pat. No. 9,421,305 (2016), "Aligned Scaffolding System for Skeletal Muscle Regeneration." The patent discusses an anisotropic muscle implant made of electrospun fibers oriented along a longitudinal axis and cross linked to form a scaffold. Cells are seeded on the fibers to form myotubes. The fibers may be formed from natural polymers and/or synthetic polymers. Natural polymers include, for example, collagen, elastin, proteoglycans and hyaluronan. Synthetic polymers include, for example, polycaprolactone (PCL), poly(D-L-lactide-co-glycolide) (PLGA), polylactide (PLA), and poly(lactide-co-captrolactone) (PLCL). The fibers also may include hydrogels, microparticles, liposomes or vesicles. When blended, the ratio of natural polymer to synthetic polymer are between 2:1 and 1:2 by weight.

Electrospun scaffolds for generation of soft tissue replacements are described by Sensini et al., "Biofabrication of Bundles of Poly(lactic acid)-collagen Blends Mimicking the Fascicles of the Human Achilles Tendon," Biofabrication 9 (2017) 015025, doi.org/10.1088/1758-5090/aa6204. Two different blends of PLLA and collagen were compared with bundles of pure collagen.

Yang et al., US Published Patent Application 2014/0011416 (2014), "Three Dimensionally and Randomly Oriented Fibrous Structures," describes a method for producing randomly and evenly oriented three dimensional fibrous structures via electrospinning. It describes electrospinning a dope comprising one or more polymers, such as collagen, polylactic acid (PLA) and others, a solvent and a surfactant. The surfactant can be one or more of a diverse group including anionic surfactants, cationic surfactants, nonionic surfactants and zwitterionic surfactants. The spinning dope also includes one or more of a variety of solvents including acetic acid, chloroform, dimethyl sulfoxide (DMSO), ethanol, methanol and phosphate buffered saline.

And Dong et al., U.S. Pat. No. 8,318,903 (2012), "Benign Solvents for Forming Protein Structures," describes methods for forming various protein structures by dissolving a protein, such as collagen, in a benign solvent comprising water, alcohol and salt. It also describes conventional electrospinning techniques.

Elamparithi et al., Indian published patent application IN640CHE2013 (2013), "A Method for Preparing a Three-Dimensional Collagen Fiber Mat Using Benign Solvent and Products Thereof," describes a three dimensional, electrospun collagen mat prepared with a combination of acetic acid and DMSO as an environmentally benign solvent system. Another article by Elamparithi and colleagues uses the solvent system in a process of forming electrospun gelatin. See, for example, "Gelatin Electrospun Nanofibrous Matrices for Cardiac Tissue Engineering Applications," International Journal of Polymeric Materials and Polymeric Biomaterials 66(1):20-27 (2017).

SUMMARY OF THE INVENTION

The invention relates to a method for producing an implantable biopolymer scaffolds for use to contribute to, encourage, facilitate and support the repair of a soft tissue injury both biologically and mechanically, such as damage and injuries to tendons and ligaments.

Contemplated tendons that may be repaired include the Achilles tendon, rotator cuff tendon, patellar tendon, biceps tendon, and quadriceps tendon. Contemplated ligaments than may be repaired include the anterior talofibular ligament, medial collateral ligament, posterior cruciate and the ligaments of the spine and temporomandibular joint.

Biopolymer scaffolds according to the invention are produced by dissolving a biopolymer, and optionally a bio-acceptable polymer, in a DMSO solvent system. Preferred solvent systems are mixtures of about 40 to 100% by volume of dimethylsulfoxide (DMSO) and about 0 to 60% by volume of a solvent selected from the group consisting of ethanol, tetrahydrofuran and acetic acid. After preparing a solution of the biopolymer in the solvent system, biopolymers are generated and collected.

In certain embodiments of the method and certain embodiments of the biopolymer scaffold, the biopolymer fibers are formed of collagen, either entirely, or in a range of about 10 to 100% by weight. The use of 100% collagen in the biopolymers is preferred. Correspondingly, when 100% collagen is not utilized, about 0 to 90% by weight of a bio-acceptable polymer is also used to generate the fibers. Contemplated bio-acceptable polymers are PDLA, PDLLA, PLGA and mixtures thereof. Contemplated types of collagen include type I collagen, atelocollagen, telocollagen, recombinant human collagen and mixtures thereof. And high molecular weight PDLLA also is preferred, for example, PDLLA having an inherent viscosity of about 1.6-2.4 dl/g.

In various embodiments of the invention, the biopolymer fibers are generated by various techniques that including electrospinning and pneumatospinning.

Other aspects of the invention include the use of such implantable biopolymer scaffolds to encourage, facilitate and support the repair of a soft tissue injury. Such scaffolds may be formed of one sheet of the biopolymer fibers mentioned above or from a plurality of sheets. The fibers range in composition as described above.

Preferred embodiments of the invention reflect these chemical components, techniques for generating biopolymer fibers, and post-processing steps for the scaffolds that include vacuum drying to remove residual solvents and annealing of the sheets and scaffolds while restraining them from shrinking or while mechanically drawing them along the axis of their alignment.

Accordingly, embodiments of scaffolds processed as disclosed, possess an average porosity of about 50 to 150 microns as determined by mercury porosimetry, and in other embodiments about 80 to 120 microns or 100 microns. These embodiments also may have an absorbance of about the scaffold's weight in blood in about 5 min and an absorbance of about twice its weight in blood in about 20 minutes when measured in vitro; an average fiber diameter in the range of about 150-4,500 nm, preferably about 300-3,000 nm, more preferably about 500-2,000 nm and most preferably about 700-1,200 nm; substantial in vivo cell infiltration into the scaffold within about two weeks following implantation into a subject, and in some embodiments the amount of cellular infiltration reaching to about the full thickness of the implanted scaffold; and where the average configuration of the pores and void spaces in the scaffolds is substantially in the shape of a slit relative to other configurations such as elliptical, cylindrical or random pore configurations.

Other embodiments of the implantable biopolymer scaffolds have an inner surface formed of substantially aligned biopolymer fibers and an outer surface having fibers that are not substantially aligned or are oriented randomly.

Yet other embodiments of the invention are implantable biopolymer scaffolds that are seeded with various types of cells. Contemplated cells include tenocytes, myoblasts, myocytes, satellite cells, fibroblasts, osteoblasts, chondrocytes, and vascular cells, such as endothelial cells and stem cells.

Further embodiments of the invention include the production of biopolymer implants in useful dimensions and configurations and packaged in a sterile container.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a partially torn tendon. FIG. 1B shows a suture repair. FIG. 1C shows an implant wrapped around repair. FIG. 1D shows an implant sutured in place.

FIG. 6A shows an H&E histology of subcutaneous implants of collagen/biopolymer electrospun from hexafluoroisopropanol (HFP) at 8 weeks with low cell infiltration; FIG. 6B shows an H&E histology of subcutaneous implants of collagen/biopolymer electrospun from DMSO at 2 weeks; and FIG. 6C depicts FIGS. 6A and 6B graphically. * and dashed lines in FIGS. 6A and 6B indicate and demarcate the electrospun implants, 10× magnification.

FIG. 7 shows the results of 7 day media stability testing of electrospun collagen:PDLLA scaffolds. FIGS. 7A and 7B depict the electrospun scaffold shrinkage in media and electrospun scaffold volume swell in media, respectively. DMSO:EtOH composition: 150 mg/mL 30:70 TeloCollagen:PDLLA dissolved in 65:35 DMSO:EtOH. DMSO:THF composition: 150 mg/mL 30:70 TeloCollagen:PDLLA dissolved in 75:25 DMSO:THF. HFP composition: 100 mg/mL 30:70 TeloCollagen:PDLLA dissolved in HFP. Scaffold area and volume were evaluated at days 0 (prior to incubation in DMEM at 37° C. with 5% $CO_2$), 1, 4, and 7.

DETAILED DESCRIPTION

Figure 1:
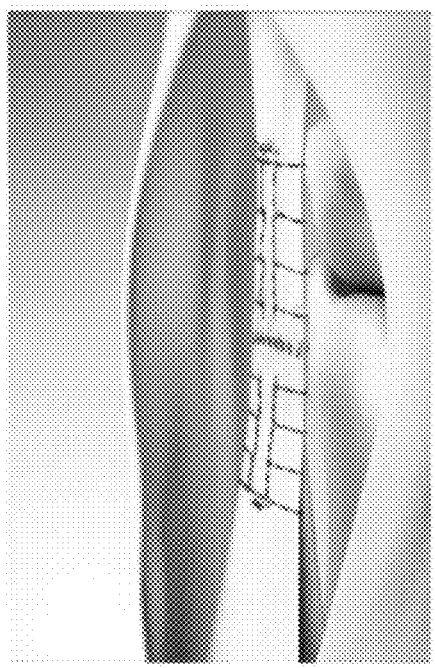
FIGS. 1A-1D show a preferred embodiment of the invention in which a biopolymer scaffold in the form of a sheet is implanted and wrapped around a partially torn tendon after a surgical suture repair and then the scaffold itself is sutured in place.
Figure 1:
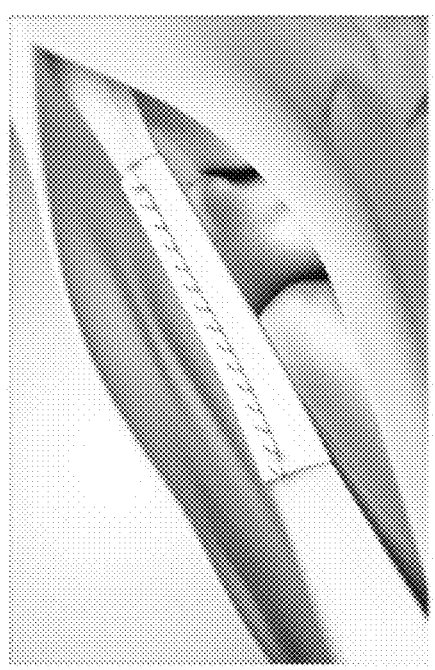
Figure 1:
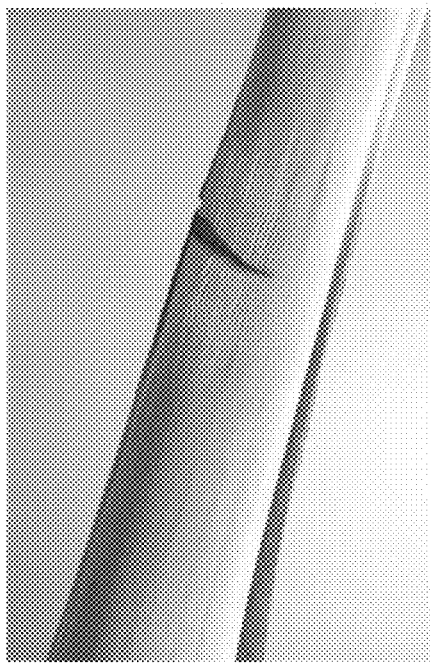
Figure 1:
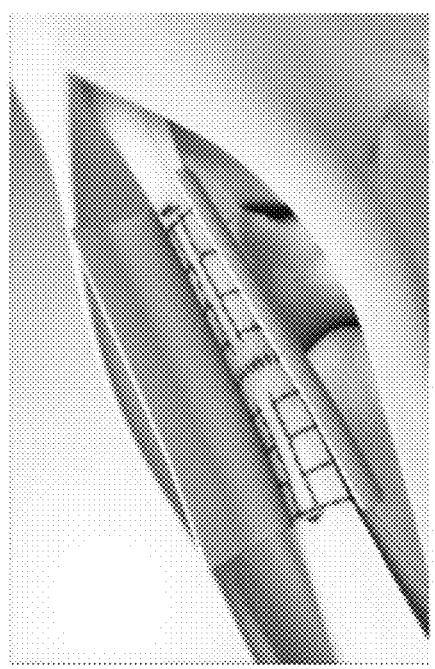

The invention relates to implantable biopolymer scaffolds and methods for their use in the management, protection and repair of soft tissue injuries. The injuries preferably involve ligaments and tendons that do not exhibit a substantial loss of tissue as a result of the injury. The implants encourage and facilitate a healing response in the area of injury. This includes the remodeling of the implant through cellular infiltration and tissue ingrowth, the deposition of collagen fibers, as well as vascularization and resorption of the implant by the treated subject. FIG. 1 shows a preferred embodiment of the invention in which a biopolymer scaffold in the form of a sheet is implanted and wrapped around a partially torn tendon after a surgical suture repair and then the scaffold itself is sutured in place.

The invention also relates to methods for producing a biopolymer scaffold, meaning a construct formed from biopolymers and bio-acceptable polymers. Such constructs are preferably substantially aligned fibers formed into layers, mats, sheets and tubes, and may be used as an implant for the management, protection and repair of injuries to soft tissue injuries such ligaments and tendons.

A method of the invention dissolves a biopolymer, and optionally a bio-acceptable polymer, in a DMSO solvent system comprising about 40 to 100% by volume of dimethylsulfoxide (DMSO) and about 0 to 60% by volume of a solvent selected from the group consisting of ethanol and tetrahydrofuran (THF) to form a biopolymer solution; generates biopolymer fibers from the biopolymer solution; and collects the biopolymer fibers to form a biopolymer scaffold.

Biopolymers

Biopolymers which may be used in a method of the invention to produce a biopolymer scaffold are proteins which are components native tissues biological structure and extracellular matrices. Contemplated biopolymers are naturally occurring, protein-based macromolecule natively found in connective and other soft tissue and in the extracellular matrix, such as collagen, elastin, extracellular matrix proteins, fibrin, fibrinogen, gelatin and laminin, and combinations thereof. Also contemplated are the use of recombinant and chemically modified forms of the foregoing protein-based macromolecules, as well as collagen from marine sources such as jellyfish, sea cucumber and cuttlefish.

A preferred biopolymer is collagen. Type I collagen used for biocompatible scaffolds according to the present invention generally are extracted from mammalian tissues, particularly bovine and porcine tendons, although recombinant collagen also may be used. Acellular human dermis is sometimes used as a source of collagen.

Type I collagen has been utilized and commercialized in both research and clinical grade products in two common forms. The more common collagen variants, produced with acid and enzymatic digestion of a tissue with pepsin, are a form of collagen referred to as "atelocollagen," as it lacks the end-terminal regions of the collagen protein (terminal peptide sequence of "DEKSTGISVP vs. pQLSYGYDEKSTGISVP), whereby the telopeptides are cleaved to aid in recovery of collagen from the parent tissue. Less commonly, collagen is solubilized in mild acid to collect the collagen in solution, maintaining the telopeptides in the monomers of collagen, known as "telocollagen."

Acid-soluble (telocollagen) and pepsin-soluble (atelocollagen) freeze dried collagen are appropriate starting materials for use in a method of the invention. A preferred GMP-grade, type I collagen from bovine corium is available in its native form from Collagen Solutions, http://www.collagensolutions.com/products/medical-grade-collagen. Collagen is also available from other suppliers and from various species, for example, Sigma-Aldrich, http://www.sigmaaldrich.com/life-science/metabolomics/enzyme-explorer/learning-center/structural-proteins/collagen.html.

A preferred scaffold according to the invention is comprised of 100% biopolymer without including a bio-acceptable polymer. Other preferred embodiments produce scaffolds that are mixtures or blends of biopolymer together with one or more bio-acceptable polymers.

Bio-Acceptable Polymers

A biopolymer scaffold may be produced according to the invention using a mixture of a biopolymer and a bio-acceptable polymer. Incorporating a bio-acceptable polymer presents a means to modulate overall graft material properties such as strength, fiber size, stability and degradation characteristics, while reducing overall graft cost for possibly little loss in cytocompatibility. A wide variety of bio-acceptable, for example, biodegradable and bioactive, polymers have been considered for use in soft tissue repair, alone or in blends with other polymers, and sometimes including components of native tissue such as the proteins recited above. Useful and improved biomechanical and biodegradability properties result from the blended combination of such proteins with various bio-acceptable polymers, for example by combining collagen with polylactic acid, including both its L- and D-isoforms, and particularly so with its racemic mixture referred to as poly-DL-lactide or PDLLA.

The PLLA isoform alone is relatively strong but brittle rather than elastic. It persists in vivo for about 36 to 48 months. A preferred PLLA for some applications of supporting injured soft tissue is available from Sigma Aldrich. http://www.sigmaaldrich.com/content/dam/sigma-aldrich/articles/material-matters/pdf/resomer-biodegradeable-polymers.pdf. However, PLLA is insoluble in DMSO, so the use of this bio-acceptable polymer and a base solvent should be assessed on a case-by-case basis and appropriate solvents other than DMSO generally should be utilized. The PDLA isoform is more elastic and not as brittle, and typically lasts for 12 to 18 months in vivo. A preferred PDLA is available from Sigma Aldrich. http://www.sigmaaldrich.com/catalog/product/SIGMA/67122?lang=en&region=US. PDLLA generally lies between PLLA and PDLA in terms of strength and stability, and in terms of lifespan in vivo is in the range of about 18 to 36 months, which generally is long enough to be resorbed and short enough to avoid encapsulation. PDLLA is an amorphous polymer formed via polymerization of a racemic mixture of L- and D-lactides. The precise composition of the polymer determines its mechanical properties and hydrolysis characteristics.

PDLLA with an inherent viscosity ranging from about 0.5-5 dL/g may be used to produce biopolymer scaffolds according to the invention. A PDLLA having a relatively higher average inherent viscosity, about 1.5-6 dL/g, is a preferred bio-acceptable polymer, more preferably about 4-5 dL/g, 5 although PDLLA with a lower inherent viscosity, 0.5-1.3 dL/g, can be used when a lower peak stress is appropriate. A preferred PDLLA, having an inherent viscosity of 1.6-2.4 dL/g, is available from Polysciences, http://www.polysciences.com/default/polydl-lactic-acid-iv-20-28dlg. A lower inherent viscosity PDLLA (IV of 1.3-1.7 dL/g) is available from Evonik, http://healthcare.evonik.com/product/health-care/en/products/biomaterials/resomer/pages/medical-devices.aspx. A PDLLA with even lower average inherent viscosity of 0.55-0.75 dL/g is available from Sigma-Aldrich, http://www.sigmaaldrich.com/cataloaproduct/sigma/p1691?lang=en&region=US; and PDLLA from other sources also is available. And a preferred PDLLA with a GM P level of purity is available from Corbion ("PURASORB PDL 45") with a relatively high inherent viscosity of 4.5 dL/g. http://www.corbion.com/stabadownloads/datasheets/31d/PURASORB %20PDL %2045.pdf.

Bio-acceptable polymers that may also be useful for a given product or device, or when combined with, for example, collagen, include polylactide, polycaprolactone (PCL) and poly(lactic-co-glycolic acid) (PLGA). Other useful bio-acceptable polymers are known to persons skilled in the art, for example, poly(glycolic acid), polyesters, trimethylene carbonate, polydioxanone, caprolactone, alkylene oxides, ortho esters, hyaluronic acids, alginates, synthetic polymers from natural fats and oils, and combinations thereof.

Bio-acceptable polymers used with the biopolymers may be pretreated with one or more functionalization reagents to prepare the bio-acceptable polymer for cross-linking upon generation of biopolymer/bio-acceptable polymer fibers from the biopolymer solution. For example, PDLLA can be functionalized through aminolysis to add amino groups. See, for example, Min et al., "Functionalized Poly(D,L-lactide) for Pulmonary Epithelial Cell Culture," Advanced Engineering Materials 12(4):B101-B112 (2010) at http://onlinelibrary.wiley.com/doi/10.1002/adem.200980031/abstract. Alternatively, PDLLA can be functionalized by plasma treatment to introduce carboxylic and amino groups in the matrix.

As a general approach, by way of example, PDLLA can be functionalized with OH groups prior to electrospinning. PDLLA pellets are soaked in a solution mixture of 10 mM-1M sodium hydroxide dissolved in 10-20% ethanol in milliQ (ultrapurified) water. The pellets will soak for 10-60 minutes at either room temperature or 37° C. Following incubation, the pellets will be rinsed in milliliters of distilled or more highly purified water and air dried in a biosafety hood. The functionalized PDLLA chips could then be dissolved in a DMSO solvent system, such as DMSO/ethanol, described below.

When a mixture of biopolymers and bio-acceptable polymers are used, the mixture may contain about 10 to 50% biopolymer by weight, preferably about 15 to 40% biopolymer, more preferably about 20 to 35% biopolymer, more preferably about 27.5 to 32.5% biopolymer and most preferably about 30% biopolymer with the remainder being bio-acceptable polymer. Mixture of two or more biopolymers and/or two or more bio-acceptable polymers may be used as the biopolymer and/or as the bio-acceptable polymer components.

A preferred biopolymer to bio-acceptable polymer mixture contains about 10 to 50% collagen and about 50 to 90% bio-acceptable polymer by weight, preferably about 25 to 35% collagen, more preferably about 27.5 to 32.5% collagen and most preferably about 30% collagen and 70% bio-acceptable polymer by weight. Type I collagen is preferred and a lactide polymer, particularly PDLLA, is preferred as the bio-acceptable polymer. Telocollagen and atelocollagen are also preferred in such mixtures. A preferred composition is about 30% type I bovine dermal collagen and about 70% PDLLA that is not chemically crosslinked during post production processing. Such compositions exhibit desired biomechanical performance and biostability parameters.

Benign Solvent Systems

A method of the invention dissolves a biopolymer, and optionally a bio-acceptable polymer, in a solvent system, preferably dimethylsulfoxide (DMSO), to form a biopolymer solution. A preferred DMSO solvent system contains about 100% by volume of DMSO. Other embodiments contain about 40 to 100% by volume of dimethylsulfoxide (DMSO) and about 0 to 60% by volume of a solvent such as the monohydric alcohols, cyclic ethers, branched chain ethers and their chlorinated and fluorinated derivatives and esters and combinations thereof. Contemplated solvents include methanol, ethanol, propan-2-ol, butan-1-ol, pentan-1-ol, hexadecane-1-ol and other saturated straight and branched chain hydrocarbons containing a single hydroxyl functional group, and combinations thereof. Preferred cyclic ethers include oxalate (otherwise known as "tetrahydrofuran" or "THF"), oxetane, and combinations thereof. Preferred solvents are ethanol and tetrahydrofuran (THF), and mixtures thereof, when electrospinning is the technique used to produce the biopolymer scaffolds. DMSO and acetic acid, and mixtures thereof, are preferred when pneumatospinning is the technique used to produce the biopolymer scaffolds.

The DMSO solvent systems used in the methods of the invention are "benign" solvent systems. They are solvents capable of dissolving the biopolymers and bio-acceptable polymers making up a biopolymer scaffold, and are either generally recognized as safe by the US Food and Drug Administration or otherwise causes minimal risk to the health of a human or other mammalian subject relative to other conventional solvents used in electrospinning techniques to produce related implantable scaffolds, for example, such as 1,1,1,3,3,3 hexafluoro-2-propanol (HFP).

DMSO is a polar chemical that readily dissolves various biological molecules such as proteins and nucleic acids. In general, DMSO has been shown to be a versatile chemical that enhances biological function such as membrane penetration, membrane transport, anti-inflammation, vasodilation and much more. Moreover, DMSO is a solvent that can be used in a solvent system or solvent blend with ethanol and THF. It exhibits a relatively low toxicity and is considered to be a safer option as compared, for example, to HFP, which is a common solvent used for electrospinning collagen and other polymers. Because of HFP's comparative toxicity, its presence in an electrospun material or implant adversely impacts biocompatibility after implantation. As is known to persons skilled in the art, DMSO is hygroscopic, so minimizing exposure to water is important. DMSO solutions for preferred solvent systems also have a relatively low water content.

DMSO solvent systems for producing biopolymer scaffolds according to the invention preferably contain about 100% DMSO. Other preferred embodiments which contain DMSO and a solvent contain about 40 to 100%, more preferably about 50 to 99%, 55 to 95% or about 60 to 90% and most preferably about 70 to 85%, 75 to 85% or about 80% DMSO by volume and about 0 to 60%, more preferably about 1 to 50%, 5 to 45% or about 10 to 40%, and most preferably about 15 to 30%, 15 to 25% or about 20% by volume of a solvent selected from ethanol and tetrahydrofuran (THF). Ethanol is hygroscopic and typically kept sealed to minimize moisture content. THF is flammable and highly volatile. Exposure to air (that is, oxygen) should be avoided to reduce the possibility of peroxide buildup. Absolute ethanol is the preferred form of ethanol. When using THF, most preferred is 25% and when using ethanol, most preferred is 35%.

DMSO solvent systems used in a method of the invention may be prepared by simple mixing or other means known in the art. For example, combining an appropriate amount of DMSO and either THF or ethanol in a 20 mL scintillation glass vial, and mixing them by gently swirling or by pipetting the mixed solution up and down until solvents are blended. The mixed solutions should be stored in airtight vials and inside a fume hood or other similar device. Long term storage is not recommended, as possible evaporation will result in changes in solution concentrations. Persons skilled in the art will be able to utilize these and other benign solvent systems.

Biopolymer Solutions

In a method of the invention, a biopolymer solution is prepared by dissolving a biopolymer or a biopolymer/bio-acceptable polymer mixture in a DMSO solvent system, for example 30% (300 g/mL) collagen and 70% (700 g/mL) PDLLA by weight (w/w). The biopolymer or biopolymer/bio-acceptable polymer mixture may be dissolved in the DMSO solvent system using means known in the art. For example, a solution of DMSO and ethanol or DMSO and THF is pre-mixed to make the DMSO solvent system prior to adding the biopolymer and bio-acceptable polymer, if present. Next, the biopolymer such as collagen is added at the same time as any bio-acceptable polymer, which can be either vortexed together at room temperature or left sitting at room temperature and inverted by hand prior to generating biopolymer fibers, for example by electrospinning. Generally, bio-acceptable polymers require vortexing or agitation to dissolve whereas collagen alone does not. Alternatively, a biopolymer such as collagen and bio-acceptable polymers can be dissolved separately and brought together or blended together and dissolved at one time.

Production of Biopolymer Fibers and Biopolymer Scaffolds

The biopolymer fibers after being generated from solution are then collected to form a biopolymer scaffold. The biopolymer fibers and biopolymer scaffold may be composed of a single biopolymer, a mixture of biopolymers, a mixture of a biopolymer and a bio-acceptable polymer, or a mixture of two or more biopolymers and one or more bio-acceptable polymers. Biopolymers and bio-acceptable polymers, together with their preferred embodiments, are discussed above. The biopolymer fibers and scaffolds each represent separate embodiments of the invention and exhibit reduced or comparable amounts of shrinkage relative to scaffolds prepared with conventional solvent techniques as well as improved swelling characteristics when wetted with various liquids after production, for example blood and other biological fluids to which the scaffolds are exposed after implantation in a subject for medical purposes.

Biopolymer fibers and scaffolds of the invention may be produced by various techniques. Electrospinning and pneumatospinning are preferred. Electrospinning offers relatively more control of both collagen microfiber diameter and for controlling the ordering of the fibers in two dimensions. Electrospinning, however, has limited ability to produce thick three-dimensional materials due to electrical insulation of the collector, typically producing biopolymer sheets of about one millimeter or less in a single layer. This limitation is not present with pneumatospinning which has a theoretically unlimited thickness. We may also e-spin with salts such as sodium acetate in the biopolymer mix and the pH of DMSO can be lowered through a variety of methods such as adding HCl or acetic acid to the DMSO, in order to adjust or improve the strength or crosslinking of resultant scaffolds, as may be determined by a person skilled in the art.

Electrospinning

Figure 2:
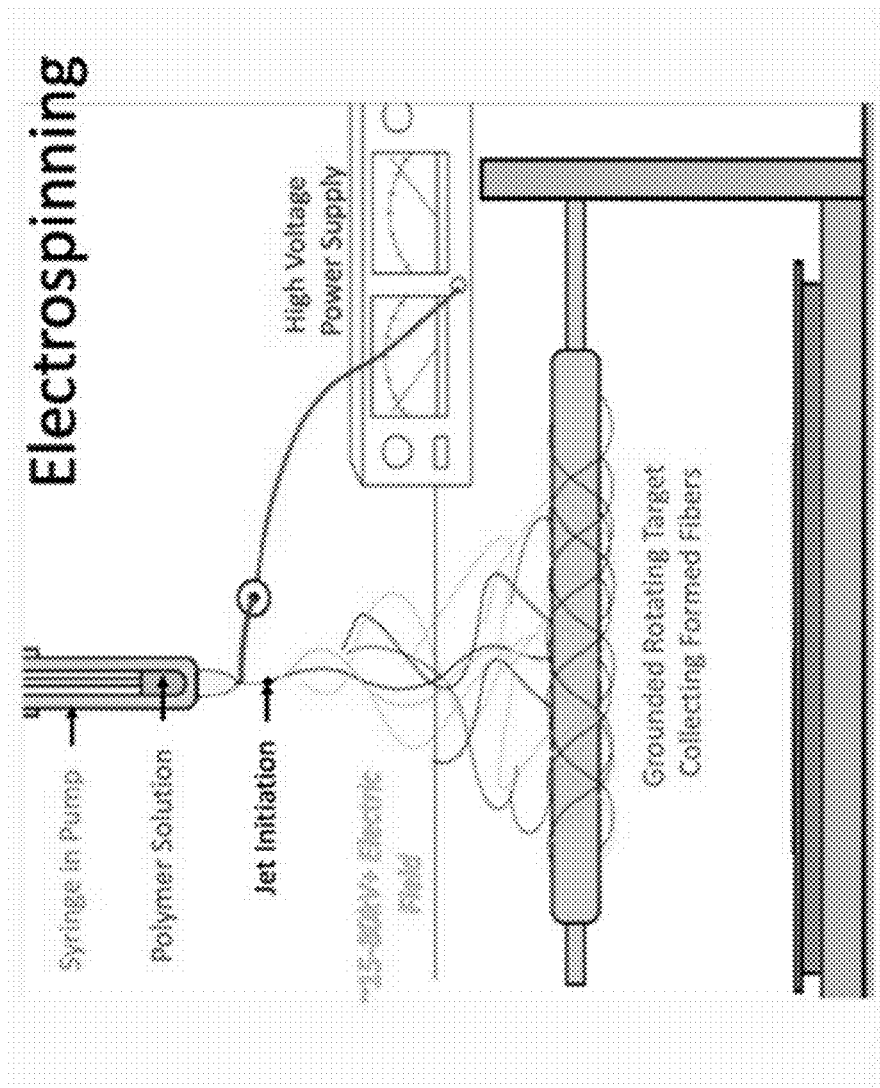
FIG. 2 shows a general illustration of the electrospinning technique described herein.

Electrospinning is a preferred processing technique to generate biopolymer fibers from the biopolymer solution. FIG. 2 shows a general illustration of the electrospinning apparatus described herein. Other approaches to separating the blend from the solvent system will be known to persons skilled in the art, for example, pneumatospinning, extrusion, cold drawing or casting.

Electrospinning is a fiber production technology that draws charged threads of polymer solutions or polymer melts into fibers of various diameters and lengths. Electrospinning shares characteristics of both electrospraying, conventional solution dry spinning and extrusion, or pulltrusion of fibers. Electrospinning of collagen has been widely described as a one-step process for the formation of fibrous materials that mimic native tissue structure. Biopolymer scaffolds in the form of sheets may be produced by electrospinning biopolymer fibers onto a high-speed drum (at a surface speed of around 1-20 m/s). As mentioned below, the biopolymer scaffolds can be vacuum dried after electrospinning to remove residual solvents. For example, the scaffolds can be dried at a temperature of about 30-37° C. to remove residual processing solvents. Electrospinning equipment is conventional and readily available. Generally, fibrous sheets are readily peeled or removed from the drum as large sheets which can then be cold-drawn or cut or folded to produce scaffolds of various dimensions.

Pneumatospinning

Pneumatospinning is another preferred fiber and scaffold production technology useful to produce biopolymers and implants according to the invention. This embodiment of the invention provides an original method of collagen microfiber production and assembly using high velocity air (pneumatospinning) to generate anisotropic and isotropic scaffolds, or useful for collagen coatings on other devices. As illustrated in the accompanying FIGS. 3A to 3D, scaffolds are produced by ejecting biopolymer solution through an injector 702 (airbrush) into the internal post fiber collector 706 as the internal post fiber collector 706 rotates with respect to the position of the nozzle 704 of the injector 702.

A. Internal Post Fiber Collector

In one example implementation of the invention, the collector 706 is substantially an open cylinder in shape with a hollow interior portion 709 bounded on its circumference by a collector wall 716. In other example implementations of the invention, the collector can have other curvilinear planes and/or can be closed at an end opposite the injector.

Figure 3:
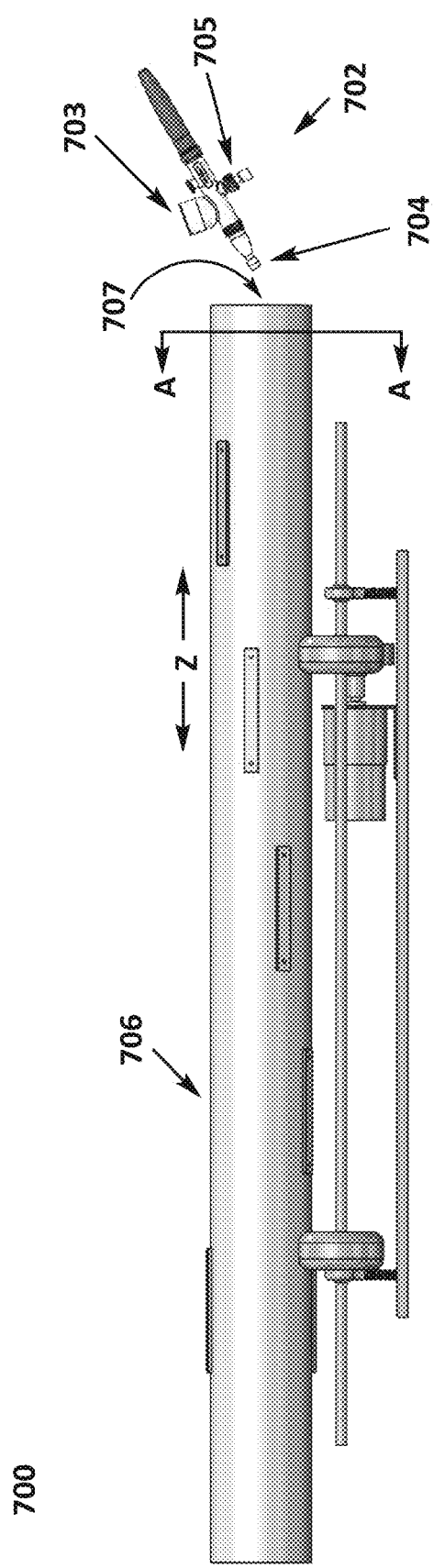
FIGS. 3A-3D depict a preferred embodiment of the pneumatospinning device of the claimed invention.
Figures 3, 3B:
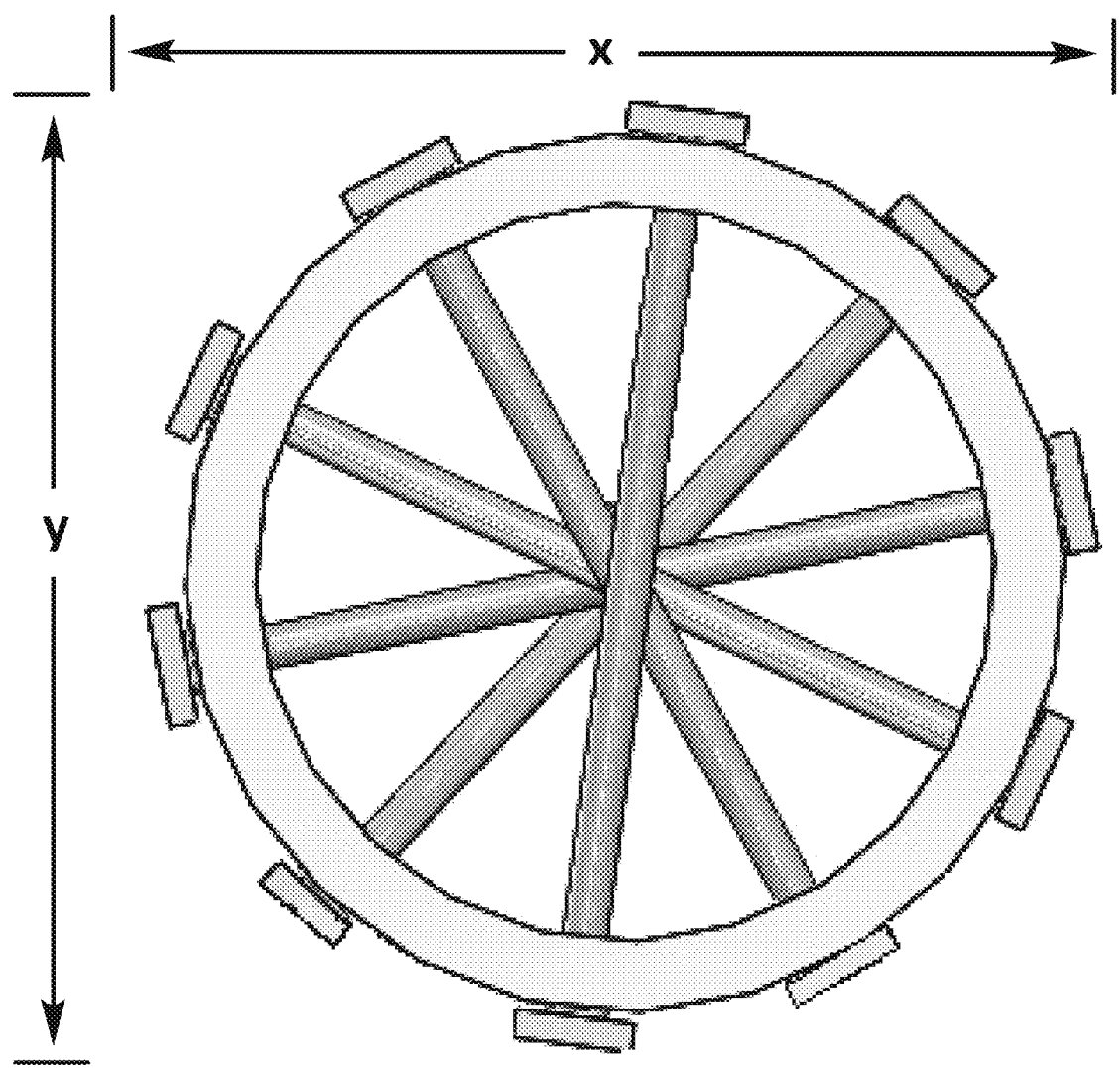
Figures 3, 3C:
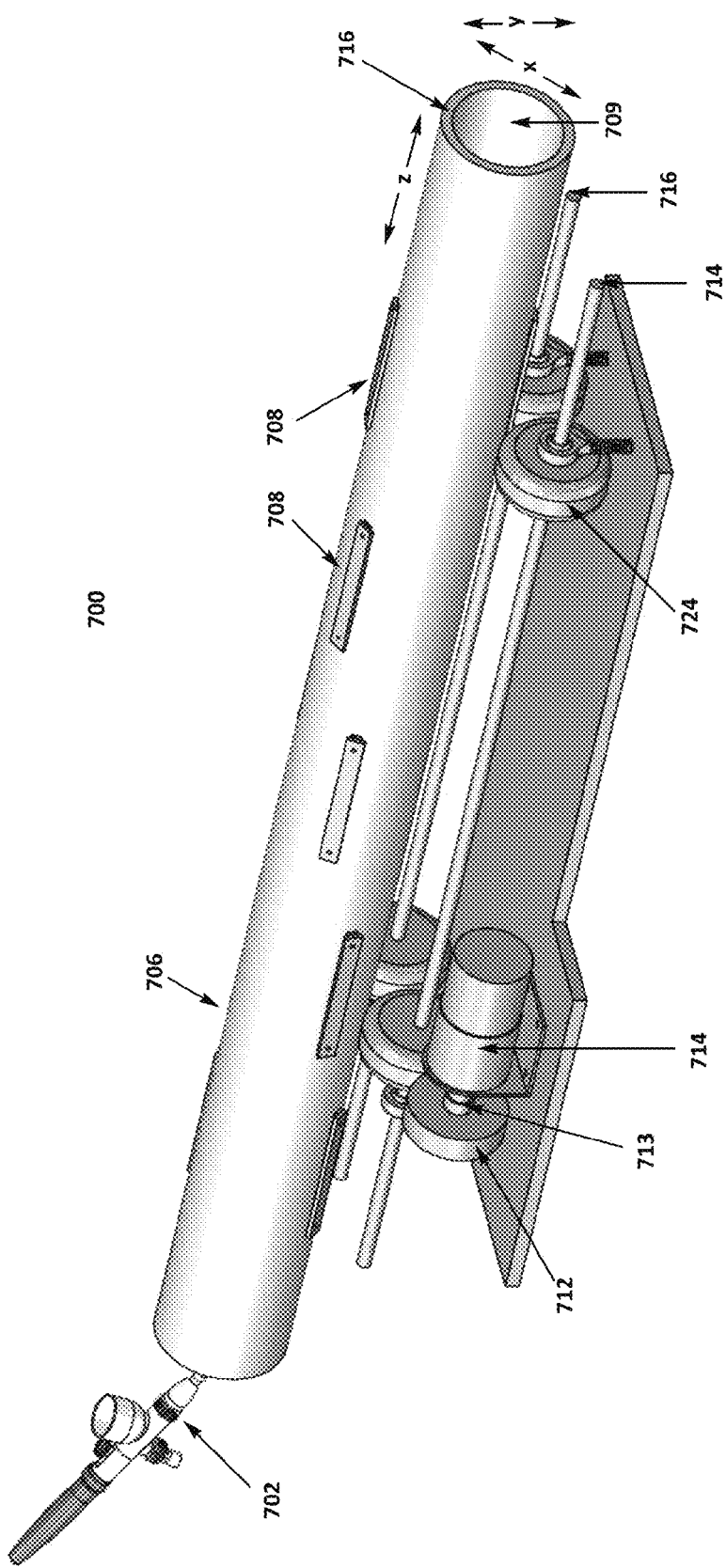
Figure 3D:
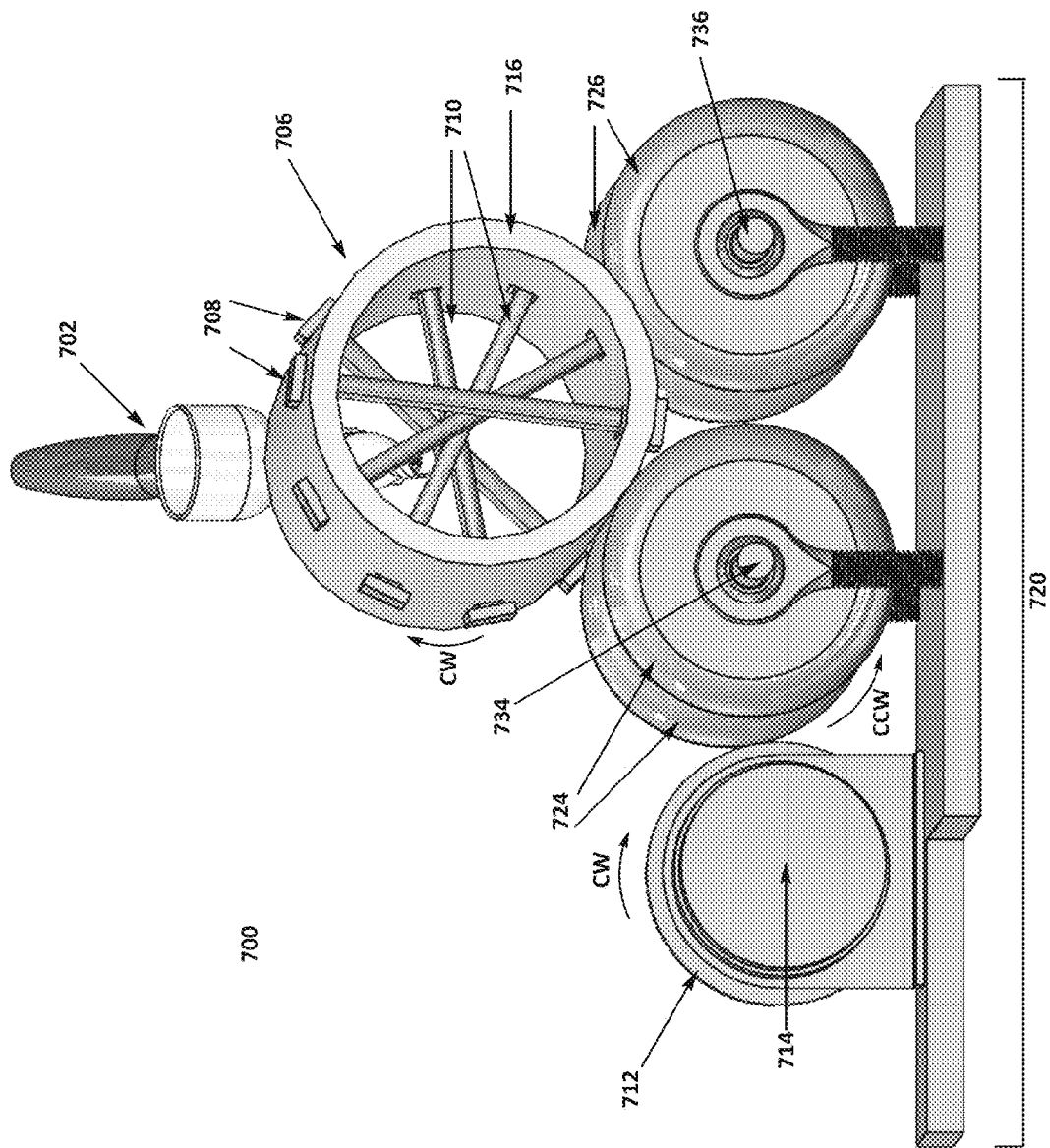

As shown in FIGS. 3A-3D, fiber collector 706 can be substantially an open cylinder in shape with internal spokes 710 positioned axially in the interior portion 709 of the collector 706. The spokes 710 can be coaxial in the same X-Y plane within the collector 706 or can be arranged in a spiral array staggered throughout the length of the collector 706 as shown in FIGS. 3A and 3C, where spoke holders 708 are positioned at different points along the length (Z-direction) of the collector 706. The spokes 710 can be removably attached to the collector 706. In one example implementation of the invention, the spokes 710 can be attached/secured to the collector 706 on the outside of collector wall 716 using spoke holders 708. The spokes 710 can be removed from the collector 706 at the end of the collection process to access the biopolymer scaffold(s). In other example implementations, the spokes 710 can be secured to the collector wall 716 on the interior portion 709 of the collector 706 and can also be removed to facilitate access to the biopolymer scaffold(s) at the end of the collection process. The spokes 710 extend across the interior diameter of the collector 706. The spokes 710 can have a number of different cross-sectional shapes, including rectangular, circular, and oval, and can have a bladed cross section as well. The relative size (e.g., diameter, cross-sectional area, etc.) of the spokes can be selected based upon the biopolymer used, the size and shape of the scaffold or grafts to be collected, and other considerations.

B. Injector

As shown in FIG. 3A, the injector 702 includes a biopolymer port 703 that receives a biopolymer, such as a collagen in acetic acid, for example. Injector 702 drives the biopolymer with regulated compressed gas, which is introduced into the injector 702 via compressed gas input 705. The injector 702 drives the biopolymer through nozzle 704 into a rotating fiber collector 706 used to collect the biopolymer scaffold(s).

C. Rotation Components

In the FIGS. 3A-3D, the apparatus 700 uses rotation components 720, including drive motor 714, drive wheel 712, first roller axle 734, first roller wheels 724, second roller axle 736, and second roller wheels 726, to rotate the fiber collector 706. As the injector 702 ejects biopolymer solution into the collector 706, the injector 702 can be moved relative to the cross-section A-A of the collector 706 as shown in FIGS. 3A and 3B. For example, the injector 702 can be moved in the X-direction with respect to the circular cross section of the collector, in the Y-direction with respect to the circular cross section of the collector 706, and in the Z-direction with respect to the circular cross section of the collector 706. The injector 702 may be moved in any combination of the X, Y, and Z directions as well.

Rotation components 720 cause the collector 706 to rotate about its (longitudinal) central axis (Z-direction). Drive motor 714 rotates and engages drive wheel 712, which can be positioned coaxially along drive shaft 713. Drive motor 714 can be a continuous speed motor or can be a variable speed motor as needed in the particular implementation of the invention. As drive motor 714 and drive wheel 712 rotate (clock-wise, CW, for example in FIG. 3D), drive wheel 712 engages first roller wheels 724 mounted on a first roller axle 734, which in turn rotates collector 706, which in turn rotates second roller wheels 726.

First roller axle 734 and second roller axle 736 extend longitudinally and are substantially parallel to the length (Z-direction) of the collector 706. First roller axle 734 and second roller axle 736 have first roller wheels 724 and second roller wheels 726, respectively, mounted coaxially along the central axis of the respective axles 734, 736. First roller axle 734 and second roller axle 736 are spaced apart from each other (in the X-direction) such that first roller wheels 724 and second roller wheels 726 support collector 706 as shown in the figures. A plurality of first roller wheels 724 and second roller wheels 726 can be used. As shown in FIG. 3C, first roller wheels 724 and second roller wheels 726 are positioned along their respective axles 734, 736 such that they do not hit or impair the rotation of spoke holders 708, which can extend through the wall 716 of the collector 706. Spoke holders 708 hold the spokes 710 in position on (and within) the collector 706.

D. Component Positioning

As shown in the FIGS. 3A-3D, the injector 702 is positioned at one end of the collector 706. As the injector 702 drives the biopolymer through nozzle 704, drive motor 714 rotates drive wheel 712, first roller axle and wheels (734 and 724), and ultimately collector 706. The position of the injector 702 (and nozzle 704) in the X, Y, and Z-directions relative to the collector 706 and to the spokes 710 in the collector 706 can be controlled and varied by a plotter position controller (not shown separately) that moves the injector 702 in the X, Y, and Z-directions relative to the collector 706 and to the spokes 710 in the collector 706. Similarly, the angle (reference numeral 0) with respect to the collector inlet 707 at which the biopolymer is ejected from the nozzle 704 of the injector 702 can also be controlled and varied by the plotter position controller. The plotter position controller determines the position and angle at which the biopolymer solution is emitted/ejected through the nozzle 704 of the injector 702 into the collector 706.

The rotation speed of the collector 706 can be controlled and varied based on the relative diameters of the drive wheel 712, roller axes 734, 736, roller wheels 724, 726, and collector 706 as well as by the rotational speed of the drive motor 714 itself, using a speed controller (not shown separately). In this fashion, the pneumatospinning biopolymer scaffold manufacturing apparatus 700 of the invention can position the spokes 710 of the collector 706 at an optimal point (optimal points) in space to receive and collect the biopolymer fibers from the injector 702.

Using the pneumatospinning biopolymer scaffold manufacturing apparatus 700 in accordance with the invention, anisotropic or isotropic fibrous grafts can be collected with higher output, lower cost, and less complexity relative to electro spinning. Collagen microfiber synthesis in this fashion has many applications in medical device manufacturing, including ligament, tendon, and nerve repair as well as for applying microfibrous collagen-based coatings and other biopolymers to other materials.

In a pneumatospinning embodiment, the biopolymer solution may be the biopolymer and/or bio-acceptable polymer dissolved in a DMSO solvent system or dissolved in acetic acid. The defect-free production rate is preferably about 2 g/hr relative to 0.0625 g/hr with electrospinning of collagen as dissolved in acetic acid and has the potential to increase to at least 8 g/hr using this approach along with higher efficiency fiber collecting device engineering. Pneumatospinning is thus a markedly scalable approach to biopolymer fiber generation while requiring less specialized and less expensive equipment.

Processing of Fibers and Scaffolds

A method of the invention utilizes various optional steps for post-processing of a biopolymer scaffold. One post-processing step is to dry the biopolymer scaffold to remove residual solvent at least to levels consistent with requirements of the Food and Drug Administration. The drying may be done by, for example, air drying, vacuum drying, drying in a desiccator, lyophilization, drying under inert gas and like approaches. Preferably, the level of DMSO will be reduced to less than about 1.5% by weight of the scaffold.

Figure 4:
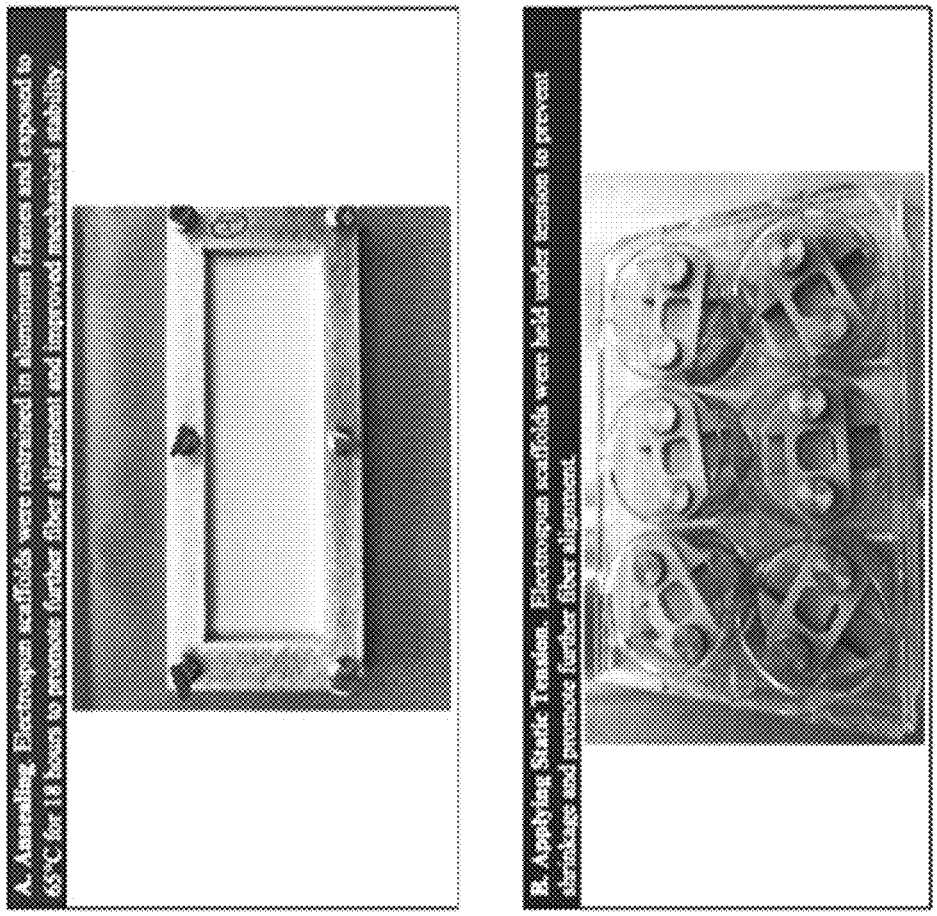
FIGS. 4A and 4B show, respectively, a biopolymer scaffold annealed in an aluminum frame, and multiple scaffolds processed simultaneously.

The post-processing of a biopolymer scaffold also may involve chemical, mechanical, physical or thermal post-processing. For example, a biopolymer scaffold produced by a method of the invention can be physically post-processed such as by thermal annealing with or without mechanical drawing, or by a mixture of annealing, drawing, and relaxation cycles. Such physical post-processing steps can be applied to temper or otherwise alter the material properties of the resulting biopolymer scaffold, such as by changing fiber diameter, fiber alignment, and void fraction or porosity of the resulting biopolymer scaffold. For example, as shown in FIGS. 4A and 4B, a biopolymer scaffold is annealed in a frame, for example made of aluminum, and optionally maintained under tension, to promote fiber alignment and improved mechanical stability. Scaffolds have been annealed in 3 different frame types with and without vacuum for up to 24 hours, specifically at 45, 55 and 65° C. The amount of tension should be sufficient to avoid or minimize scaffold shrinkage. Such annealing also surprisingly and advantageously increases the thickness of a scaffold, as much as by three fold or four fold, which facilitates the clinical use of single layer scaffold implants.

In one embodiment, the electrospun scaffolds are prepared by dissolving a blend of telocollagen (30 mg/ml) and PDL45 (70 mg/ml) for a total concentration of 100 mg/ml in 100% DMSO. The scaffolds are placed under vacuum for up to 24 hours (minimum 2 to a maximum of 24 hours).

Such scaffolds then may be annealed in fixed or un-fixed frames at temperatures of about 45, 55, and 65° C. for about 18 to 24 hours. The mechanical stability of the resulting scaffolds is significantly better when annealed at 65° C. for 18 hours. Persons skilled in the art will evaluate changes in scaffold length, which decreases, and in scaffold thickness, which increases, over time. Preferably, an annealing time from about 1 to 48 hours will be optimal, more preferably about 2 to 24 hours.

Figure 5:
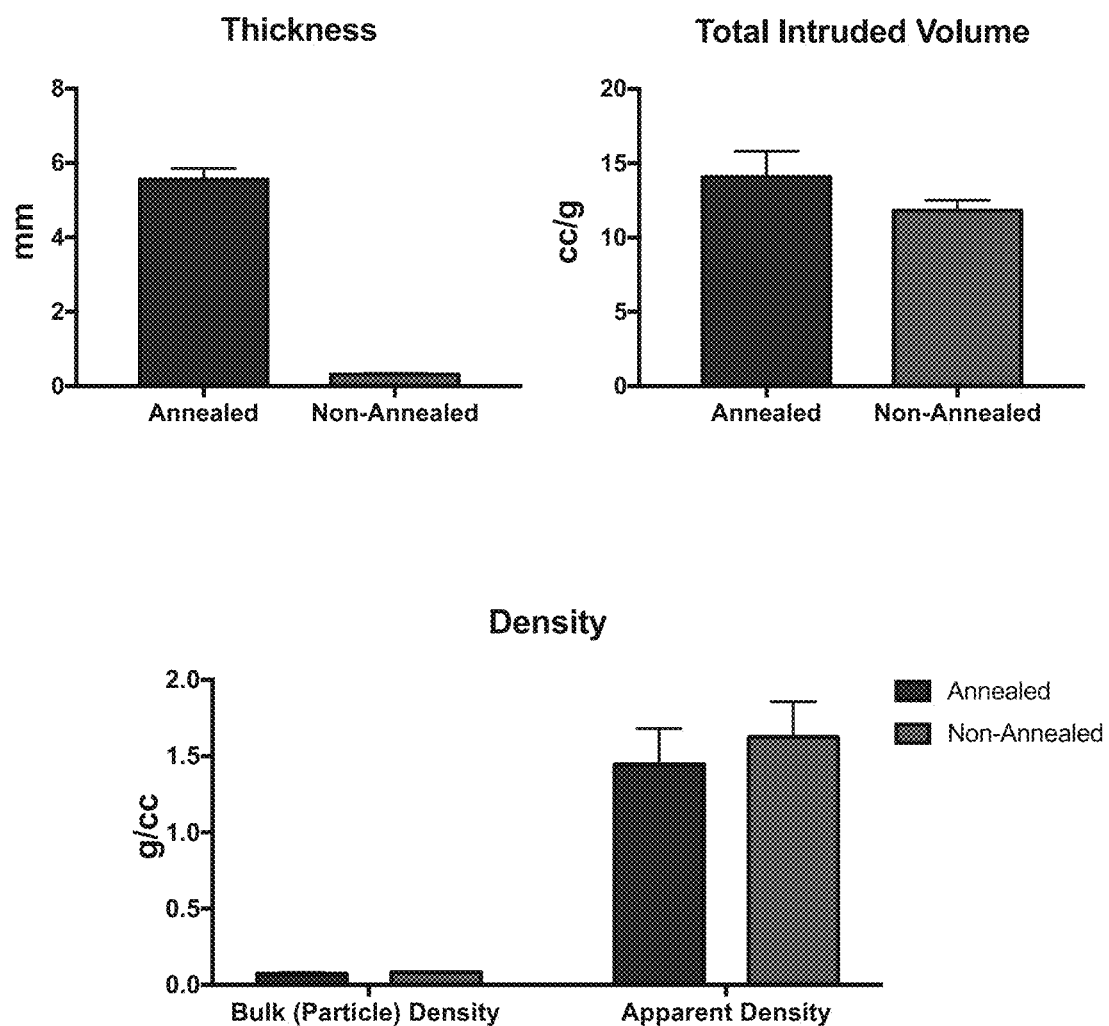
FIG. 5 shows scaffold thickness and density pre- and post-annealing.

FIG. 5 shows scaffold thickness and density pre- and post-annealing. 20 mL of solution electrospun onto a collector drum with 360 cm$^2$ surface area will result in scaffolds with the following thicknesses: The non-annealed scaffolds have an average thickness of 0.3±0.1 mm. Annealed scaffolds have an average thickness of 5.6±1.2 mm. Depending on the annealing setup, the initial scaffold thickness (non-annealed) and preferences for the use of a given scaffold, the scaffold thickness can be increased substantially.

A biopolymer scaffold of the invention optionally also may be chemically post-processed. For example, fibers within the scaffold that have been functionalized to provide amino groups prior to dissolving in the solvent system, as described above, may be crosslinked with aldehydes, in general, more specifically with small chain aldehydes, and preferably glyoxal or with other conventional crosslinking reagents after its extraction into a scaffold. For example, crosslinkers such as 1-ethyl-3-(3-dimethylaminopropyl)carbodiimide hydrochloride (EDC), N-hydroxysuccinimide (NHS), genipin, glyceraldehyde, gluteraldehyde may be used. If the bio-acceptable polymer is functionalized with carboxyl groups, then EDC and other carbodiimides may be used for crosslinking. Isocyanates react with both OH groups and amines. Therefore, isocyanate-based crosslinkers may be used to crosslink the OH groups to each other within, for example, the functionalized PDLLA (linking an OH group to another OH group) to improve media stability, strength. Isocyanates also may be used to link collagen to OH groups in functionalized PDLLA via the $NH_2$ group (that is, amine group) from the collagen. Additionally, photo-crosslinkers can be used.

Physical Characteristics of Biopolymer Fibers and Biopolymer Scaffolds

When generated from a DMSO solvent system according to the invention and processed as described in this specification, the biopolymer fibers and the biopolymer scaffolds which they form have novel and unexpected properties and characteristics not seen with other biopolymer fibers and scaffolds prepared by other means and methods.

Biopolymer fibers generated from the DMSO solvent system according to the invention range in diameter from about 150-4,500 nm, preferably about 300 nm to 3,000 nm, more preferably about 500 nm to 2,000 nm and most preferably about 700 nm to 1,200 nm.

Biopolymer scaffolds produced according to the invention have advantageous strength profiles based on several contributing factors, including the solvent system, choice of bio-acceptable polymer, and the various post-processing steps as discussed in this specification. For example, when considering selection of the solvent system, differing ratios of DMSO:THF produced significantly differing mechanical strength profiles, with a ratio of 75:25 DMSO:THF being significantly stronger than other ratios. See Table 2 in Example 7 below. Similar results were also seen with increasing ratios of DMSO:EtOH, such that increasing relative DMSO concentrations correlated with increasing strengths, with a ratio of about 80:20 DMSO:EtOH being significantly stronger than other ratios. See Table 3 in Example 7 below. Additionally, biopolymer scaffolds spun out of 100% DMSO are stronger than any scaffold spun out of a blended solvent of DMSO:EtOH or DMSO:THF. See Tables 1 and 3 in Example 7 below.

Biopolymer scaffolds produced according to the invention have a peak stress strength about 2.5 to 10 MPa. The biopolymers possess a modulus of elasticity which is substantially like that of human tendons, particularly the Achilles Tendon, which is about 35-750 MPa. Within that range, a modulus of elasticity of about 35-200 MPa for the fibers is preferred. Also, a strain to failure of 50-100% (0.5 to 1.0 mm/mm) as tensile strength as tested at 1 mm/s in hydrated condition is preferred.

The implantable scaffolds preferably possess a tensile strength of greater than about 5 MPa, a Modulus of greater than about 6 MPa and a suture pull out strength of greater than 0.64 N.

Post-processing by annealing as described advantageously increases the average void volume between the fibers within a biopolymer implant from about 5 to 10 times that of implants produced by electrospinning with conventional solvents such as HFP. For example, an annealed scaffold produced using a DMSO solvent system according to the invention will have an average pore size, determined by mercury porosimetry, of up to about 80 to 120 micrometers, more preferably about 90 to 110 micrometers and more preferably about 100 micrometers, compared with an average pore size of about 7 micrometers in a non-annealed scaffold. Persons skilled in the art will understand that this measurement technique determines porosity by applying controlled pressure to a sample immersed in mercury. The amount of pressure required to force mercury into the pores is inversely proportional to the size of the pores, such that the larger the pore the smaller the pressure needed to penetrate into the pore. The porosity of the preferred implants greatly improves cell infiltration in vivo, overcoming a longstanding, significant challenge in the field of electrospinning products for medical device use.

Additionally, the implants may be seeded with one or more cell types, including autologous, allogeneic or xenogeneic cells. Contemplated cell types include stem cells or progenitor cells such as mesenchymal stem cells from adipose, bone marrow, or other locations, and placenta derived cells such as cord blood cells and amniotic membrane cells, induced pluripotent stem cells and embryonic stem cells. Musculoskeletal cells such as tenocytes, myoblasts or myocytes or satellite cells, fibroblasts, osteoblasts, chondrocytes, and vascular cells, such as endothelial cells, also may be used. Additionally, other cells types may be utilized as appropriate to the repair of other tissue types beyond musculoskeletal tissues, such as dermal, dura mater, adipose, mammary and other tissue-specific cell types.

Fiber and Scaffold Alignment

In a preferred embodiment of the implant, the orientation of biopolymer fibers will be different on the inner face of the implant adjacent to the injured tissue and on the outer face of the implant, with a gradient or other transition zone between the inner and outer faces. For example, the biopolymer fibers may be substantially aligned on the inner face of the implant, meaning that at least about half of the fibers lying within 15 to 20 degrees of a reference in a scaffold are oriented along a common axis. This implant preferably has a gradient of less aligned fibers through the thickness of the implant toward the outer surface on which the fibers are aligned randomly or otherwise are not substantially aligned. In other embodiments, one or more inner-facing layers of a multi-layer implant contain substantially aligned fibers and one or more outer layers of the implant contain fibers that are oriented randomly or are not substantially aligned.

Referring generally to FIG. 1, the foregoing fiber configuration facilitates suturing while a scaffold or implant is being surgically implanted into a subject and also imparts improved suture retention. This configuration also provides an anti-adhesion barrier on the outer surface and improves the implant's mechanical properties off-axis, meaning off the axis of the injured tissue and off the axis of the orientation of the tissue's own longitudinal fiber components.

Substantial alignment of the fibers in a scaffold may be produced, for example, by collecting fibers on a drum as described above while it is being rotated at a relatively slow speed resulting in the random deposition of fibers. The rotation speed can be increased relatively gradually or relatively quickly up to a rapid, or even full rotation speed, to collect fibers that are deposited in substantial alignment. In one embodiment, randomly oriented fibers are collected for about six hours and then the speed of the drum is increased over the next six hours to its terminal full speed, such as about 15 m/s. Fibers may continue to be collected for an additional twelve hours. This kind of gradient in the orientation of deposited fibers provides a superior and preferred attachment for sutures. A gradient of about 25 to 33% from random to substantially aligned fibers is preferred.

Functional Characteristics of Biocompatible Scaffolds for Implantation

As described above, the present invention is directed to the use of a benign solvent system to provide synthetic fibers and related sheet-like and bundled fiber products for tissue engineering, particularly as soft tissue supports useful in the repair of damaged tendons and ligaments. For example, according to the present invention, a tissue-engineered ligament and tendon scaffold formed of collagen and a biodegradable polymer dissolved in DMSO may be used for repair of a damaged Achilles tendon.

With respect to scaffolds prepared from the fibers, the scaffold's wettability shows stability in culture media over 7 days of incubation at 37° C. at 100% humidity in 5% $CO_2$. Generally, seeded cells preferably show robust cell attachment, with more than half of the seeded cells attaching to the scaffold.

Implants according to the present invention also absorb both clotting and non-clotting blood relatively rapidly as compared with implants produced, by example, by conventional electrospinning techniques. Absorption may be determined by techniques known in the art as disclosed, for example, in Rodriguez et al., "Demineralized bone matrix fibers formable as general and custom 3D printed mold-based implants for promoting bone regeneration" in Biofabrication 8(3):035007. doi: 10.1088/1758-5090/8/3/035007 (July 2016). Annealed scaffolds were submerged in human blood to assess blood absorption kinetics. For example, a scaffold submerged in heparinized blood absorbed 13 times its weight of ACD blood (blood that clots) and a comparable scaffold absorbed 7 times its weight of heparinized blood in about 30 minutes. A preferred implant will absorb will about one to about four times its weight in blood in about 5-30 minutes in vitro.

Figure 17:
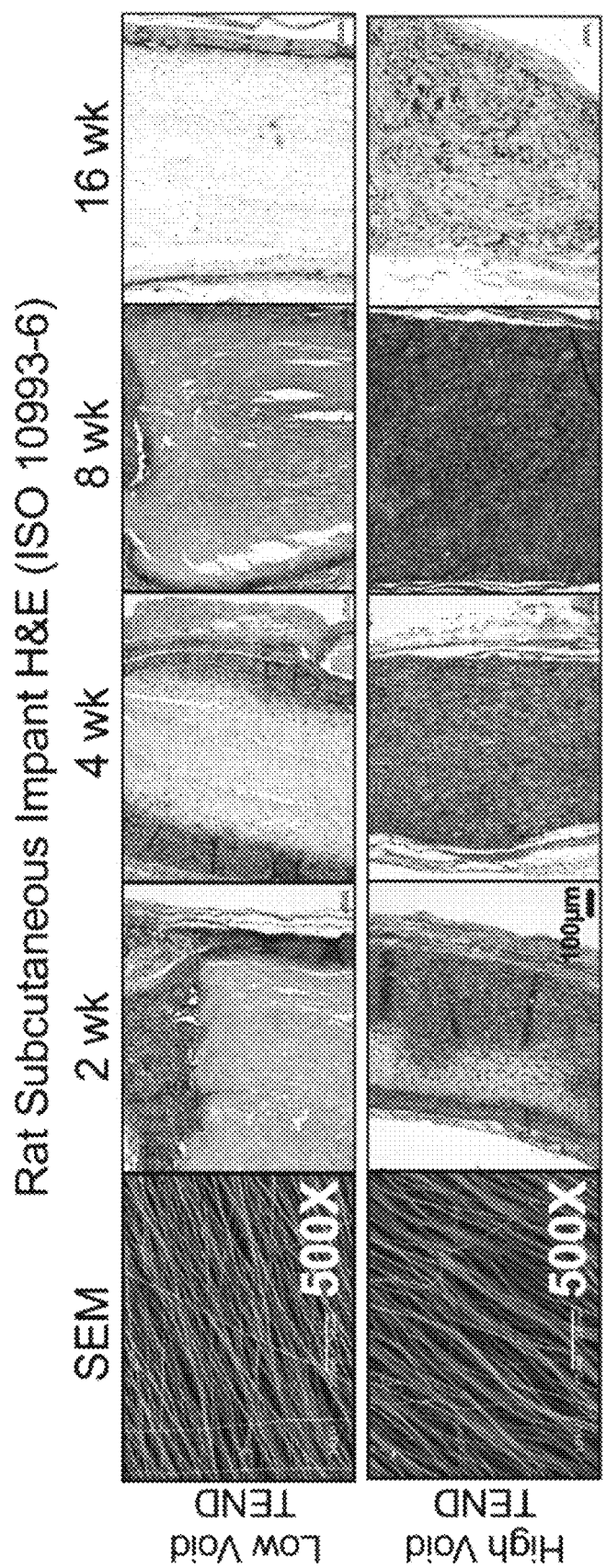
FIG. 17 shows rat subcutaneous implants with respect to cellular infiltration over 2 to 16 weeks, comparing implants with high and low porosities.
Figure 18:
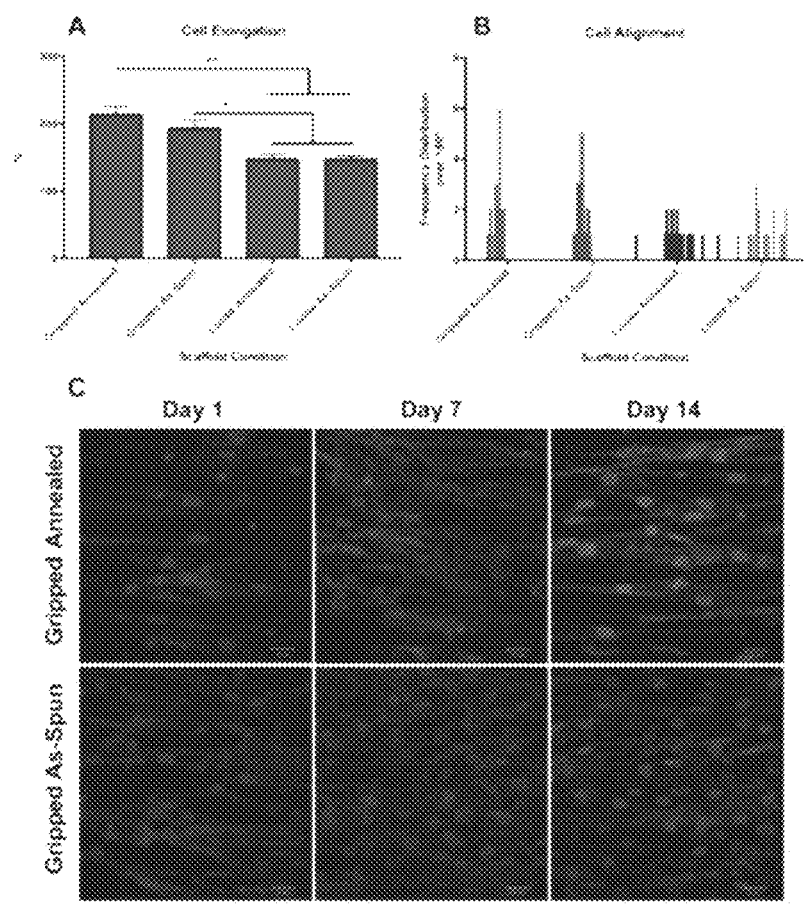
FIGS. 18A-18C illustrates tenocyte cellular alignment and cell elongation along the collagen-based microfibers.

Benign solvent systems and post processing of implants according to the present invention permit the production of scaffolds that promote cellular ingrowth that is substantially improved relative to similar grafts that have been electrospun out of HFP, a conventional electrospinning solvent, as shown in FIGS. 6A-C. As shown in FIG. 17, enhanced porosity of the scaffolds according to the invention greatly improve cellular infiltration of implanted scaffolds. Cell alignment and cell elongation are also substantially improved (FIGS. 18A-18C). Also, the initial retention of growth factors, when they are present on or embedded in an implant, is substantially more like that exhibited natively by human tendon, particularly, for example, the Achilles Tendon, as discussed in more detail below.

Biopolymer Implants for Clinical Use

Sheets of the biopolymer scaffolds optionally may be laminated through welding or suturing or sewing. In general, the sheets of biopolymer scaffolds are stacked together in layers. A brief application of heat in the range of about 30-100° C. may be applied locally to join them. Additional material also optionally may be added into welds to reinforce the implant material to aid in suture retention. Additionally, an adhesion barrier may be incorporated into the implant. Such barriers may be composed of a pure polymer backing (facing away, for example, from a tendon to which a biopolymer scaffold is to be affixed) in order to prevent extrinsic cell infiltration. The adhesion barrier layer may be electrospun, cast, foamed, extruded, or produced by other conventional techniques.

As preferred embodiments, the invention relates to biopolymer scaffolds prepared as described above and prepared for implantation into a subject (preferably mammalian and more preferably equine, canine, feline and human subjects) in the form of single or multilayer sheet-like scaffolds. In one embodiment, this scaffold is composed of around 1, 2, 3, 4, 5, 6, 7, 8, 9 or 10 or more layers of aligned biopolymer scaffold. A single layer scaffold of the invention may be around 4 cm×4 cm, 5 cm×7 cm or about 10 cm×10 cm×about 1 mm in thickness. The total thickness of the implant will range from about 0.5 mm to about 6.0 mm, preferably about 0.6 mm to about 3 mm, more preferably about 0.7 mm to about 1.0 mm and most preferably about 0.8 mm. An alternative embodiment is a multiple layer scaffold of approximately similar dimensions.

As discussed above, the implants may be produced with a randomly oriented fiber layer on its outward facing surface. Optionally, the implant also will have a small section of fibers laying in the transverse plane around the edges to provide additional biaxial support for suture retention. Also, optionally, the inner or outer surface of the implant can be marked with an arrow or other recognizable shape to distinguish the inner from outer layers.

The implants for surgical use may optionally be packaged dry in a high barrier, double foil pouch and may be frozen until being thawed before implantation.

EXAMPLES

Example 1: Preparing DMSO/Ethanol Solvents and Electrospinning Fibers of Collagen and PDLLA In 20 mL scintillation glass vials, 45 mg/mL telocollagen and 105 mg/mL PDLLA were dissolved in 6 mL DMSO:EtOH at a ratio of 65:35 for 20 hours on a shaker. (Alternatively, these ingredients may be dissolved in separate aliquots before being mixed together.) Collagen was obtained from Collagen Solutions (San Jose, Calif.) and PDLLA was obtained from Polysciences Inc. (Warrington, Pa. Cat#23976). The vials were placed on a VWR Heavy Duty Vortex Mixer (Cat #97043-562) at level 7 until the reagents dissolved, approximately 20 hours later. The solutions were then electrospun from a 6 mL plastic syringe with plastic luer having a diameter of 11.65 mm; and a 3.9 cm, 25-gauge stainless steel needle onto a drum (10 cm diameter×15.8 cm width) with six spokes that are 5 cm apart from each other using an electric motor. The drum was elevated 36 cm from the floor of the electrospinning box and the solution needle was elevated 19.5 cm above the floor of the box.

The horizontal distance from the needle tip to the plane of the drum was 16.02 cm. The sloped distance from the tip of the needle to the midline of the drum was 23 cm. Directional air flow from a fan is pointed in line with the needle tip and angled in the direction of the drum. 5 mL of solution were spun at a time. The first syringe was spun with a flow rate of 0.8 mL/hr, +15 kV was applied to the needle and −3 kV was applied to the drum. The drum speed was 350 rpm. After the first syringe was empty it was discarded, and a 5 mL syringe full of solution was attached to the luer and spinning resumed. The second 5 mLs were spun at a rate of 0.6 mL/hr, +8 kV was applied to the needle and −8 kV applied to the drum with drum speed of 350 rpm. A total of 10 mL was spun. The drum was left spinning overnight to facilitate drying of the fibers. The scaffold was removed from the spokes and placed into a desiccator with calcium sulfate desiccant.

Example 2: Preparing DMSO/THF Solvents and Electrospinning Fibers of Collagen/PDLLA In 20 mL scintillation vials, 45 mg/mL telocollagen and 105 mg/mL PDLLA were dissolved in 5 mL DMSO:THF at a ratio of 75:25 for 16 hours on a shaker. Collagen was obtained from Collagen Solutions (San Jose, Calif.) and PDLLA was obtained from Polysciences Inc. (Warrington, Pa. Cat#23976). The vials were placed on a VWR Heavy Duty Vortex Mixer (Cat #97043-562) at level 7 until the reagents dissolved, approximately 16 hours later. The solutions were then electrospun from a 6 mL plastic syringe with plastic luer having a diameter of 11.65 mm; and a 3.9 cm, 25-gauge stainless steel needle onto a drum (10 cm diameter×15.8 cm width) rotated with an electric motor and having six spokes that were 5 cm apart from each other using an electric motor.

The distances between the needle tip and drum was 16 cm. The flow rate was 0.9 mL/hr and +18 kV was applied to the needle. The drum was grounded and ran at a speed of 1000 rpm. After the first syringe was empty it was discarded, and a 6 mL syringe with 5 mL of solution was attached to the luer and spinning resumed. The spin time of 8 hours was utilized with a temperature of 23.5° C. and a relative humidity of 51%. The drum was left spinning overnight to facilitate drying of the fibers. The scaffold was removed from the drum and placed in the vacuum oven with no heat for 3 hours and then placed into the desiccator.

Example 3: Post-Extraction Treatment of Scaffolds

After extraction, the scaffolds were placed under vacuum to aid further drying and removal of residual solvents. They were then stored inside a desiccator. Generally, after extraction, scaffolds are placed under vacuum, for up to 24 hours and then wrapped in foil or placed inside a petri dish before storing.

Example 4: Preparation of Multi-Layer Collagen-Polymer Scaffolds

Two sheets that were each about 0.2 mm thick were laminated by welding with a soldering iron at 100° C. or with a short pulse of heat from an impulse sealer. Additional fibers oriented orthogonally were sealed into the weld to provide reinforcement for suture retention. Persons skilled in the art will understand how to laminate additional sheets, for example, three, four, five and six sheets may be laminated by welding in a similar manner.

Example 5: Seeding of Human Tenocytes on a Scaffold of Electrospun Fibers

Human tenocytes ($5 \times 10^4$ cells/well) are suspended in serum free media and then seeded on the scaffolds prepared according to Example 3, above. After 15, 30, and 60 minutes in culture, the plates are gently shaken, and the non-attached cells are removed. The number of non-attached cells suspended in each well are counted, and the percentage of attached cells on each scaffold disk is determined based on the total number of cells seeded. More favorable cell attachment is found compared with scaffolds prepared with conventional HFP solvent systems.

Example 6: Shrinkage and Stability Analysis of Biocompatible Sheets

Telocollagen/PDLLA electrospun sheets (dissolved in various ratios of DMSO:THF, 100:0-75:25 v/v) were tested for stability in culture media at 37° C. after about 5 days. The results demonstrated that there was 70% to 80% total area shrinkage within all the scaffolds tested (FIG. 7A). It was also shown that these scaffolds swelled up to 99% to 142% of their original size (FIG. 7B). The mechanical strength of these scaffolds was significantly reduced. See Table 1 below.

Analytical Methods Used in the Following Examples

The following methods were used to test and characterize the collagen fiber scaffolds of Examples 7-14.

Mechanical Testing:

The material properties of hydrated electrospun and pneumatospun (around 1.5 cm diameter×4 cm long) scaffolds were tested through uniaxial tensile testing using MTS Criterion, Model 42 (Eden Prairie, Minn.). All mechanical testing was performed at room temperature. Scaffold diameter and thickness were measured with precision digital calipers and recorded to calculate cross sectional area. Samples were hydrated in Dulbecco's Modification of Eagle's Medium (DMEM) (Fisher Scientific, Hampton, N.H.) for 1 hour and then loaded on the MTS machine with six sample (n=6) pulled for each group.

Scanning Electron Microscopy:

The structure of uncrosslinked pneumatospun and electrospun scaffolds was analyzed by scanning electron microscopy (SEM). Genipin crosslinked pneumatospun scaffolds were also assessed after 30 days in DMEM at 37° C., left loose (un-tensioned). Fiber formation, dimensions and matrix alignment was assessed with Orientation J feature of Image) software (NIH, Bethesda, Md.). SEM imaging was performed at Jefferson Labs (Newport News, Va.) using a JEOL JSM-6060 LV microscope (JEOL Ltd., Tokyo, Japan) with a 20 kV beam intensity.

Sodium Dodecyl Sulfate-Polyacrylamide Gel Electrophoresis:

Sodium dodecyl sulfate-polyacrylamide gel electrophoresis (SDS-PAGE) was used to compare the collagen feedstock (Collagen Solutions), pneumatospun and electrospun collagen grafts (uncrosslinked, both dissolved in acetic acid). Gradient gels (3-8%) (Invitrogen, Carlsbad, Calif.) were run at 150 kV on a Xcell SureLock (Invitrogen) gel apparatus. Gels were stained with SimplyBlue™ gel stain (Invitrogen) and then rinsed with deionized. The gel was then imaged under white light to view the protein bands.

Fourier-Transform Infrared Spectroscopy:

Fourier-transform infrared spectroscopy (FTIR) (Platinum ATR, Bruker, Billerica, Mass.) was used to assess the presence of type I collagen, as determined by the three major amide bonds characteristic at 1235, 1560, and 1650 $cm^{-1}$ wavelengths. Electrospun and pneumatospun scaffolds were compared to the starting material by assessing peak displacement and sample purity with the Essential FTIR bioinformatics software (Operant, Madison, Wis.).

Circular Dichroism:

A far UV CD (J-815, JASCO) was taken to compare the CD spectra of pneumatospun scaffolds with electrospun and starting material. CD spectra was obtained using a cuvette path length of 0.1 cm. Samples were dissolved in 50 mM acetic acid at a concentration of 0.5 mg/ml for analysis.

Statistical Analyses:

One-way analysis of variance (ANOVA) followed by the post-hoc Tukey's multiple comparison test was used to assess any difference in fiber alignment between groups. Two-way analysis of variance followed by the post-hoc Tukey's multiple comparison test was used to assess the differences in cell viability between groups and over time. An unpaired t-test was used to assess any differences in mechanical strength between the electrospun and pneumatospun collagen scaffolds. A priori, p values<0.05 were defined as significant. All tests were performed using GraphPad Prism 7, and all parameters are expressed as mean±standard error of the mean (S.E.M.).

Example 7: Inherent Viscosity of the Bio-Acceptable Polymer

Inherent viscosity (IV) of the PDLLA is correlated with overall strength of an electrospun scaffold when it is prepared using the disclosed benign solvent system. Choosing a PDLLA with a relatively higher IV leads to an increase in the peak stress and modulus of elasticity of the constructs while maintaining characteristics of native ligaments, as discussed below in Table 1.

TABLE 1

Summary of Tensile Testing Results (as statistical mean ± SD)

| | | Telocollagen:PDLLA 30:70 | | | | | |
|---|---|---|---|---|---|---|---|
| | | 150 mg/mL | | | | | 100 mg/mL |
| | | DMSO:EtOH 65:35 | | DMSO:THF 75:25 | | 100% DMSO | 100% DMSO |
| | Bovine Tail Ligaments | PDLLA IV 1.3-1.7 | PDLLA IV 1.6-2.4 | PDLLA IV 1.3-1.7 | PDLLA IV 1.6-2.4 | PDLLA IV 1.6-2.4 | PDLLA IV 4.5 |
| Peak Stress (MPa) | 5.6 ± 2.2 | 2.7 ± 0.5 | 4.0 ± 0.3 | 4.9 ± 0.9 | 8.3 ± 0.2 | 8.8 ± 0.6 | 13.3 ± 3.7 |

TABLE 1-continued

Summary of Tensile Testing Results (as statistical mean ± SD)

| | Bovine Tail Ligaments | Telocollagen:PDLLA 30:70 | | | | | |
|---|---|---|---|---|---|---|---|
| | | 150 mg/mL | | | | | 100 mg/mL |
| | | DMSO:EtOH 65:35 | | DMSO:THF 75:25 | | 100% DMSO | 100% DMSO |
| | | PDLLA IV 1.3-1.7 | PDLLA IV 1.6-2.4 | PDLLA IV 1.3-1.7 | PDLLA IV 1.6-2.4 | PDLLA IV 1.6-2.4 | PDLLA IV 4.5 |
| Modulus of Elasticity (MPa) | 6.1 ± 3.1 | 46.6 ± 22.7 | 61.4 ± 21.2 | 93.2 ± 17.0 | 186.8 ± 7.0 | 59.3 ± 8.5 | 102.9 ± 27.39 |

Scaffolds spun with differing ratios of DMSO:THF produced significantly differing mechanical strength profiles, with a ratio of 75:25 DMSO:THF being significantly stronger than other ratios. See Table 2.

TABLE 2

Summary of Tensile Testing Results (as statistical mean ± SD)

| | Telocollagen:PDLLA (IV 1.6-2.4) 30:70 150 mg/mL | |
|---|---|---|
| | DMSO:THF 65:35 | DMSO:THF 75:25 |
| Peak Stress (MPa) | 4.6 ± 0.3 | 8.3 ± 0.2 |
| Modulus of Elasticity (MPa) | 68.4 ± 10.3 | 186.8 ± 7.0 |

Similar results were also seen with increasing ratios of DMSO:EtOH, such that increasing relative DMSO concentrations correlated with increasing strengths, with a ratio of about 75:25 DMSO:EtOH being significantly stronger than other ratios and 100% DMSO resulting in the strongest scaffold. See Table 3.

TABLE 3

Summary of Tensile Testing Results (as statistical mean ± SD)

| | Telocollagen:PDLLA (IV 1.6-2.4) 30:70 150 mg/mL | | | |
|---|---|---|---|---|
| | DMSO:EtOH 50:50 | DMSO:EtOH 65:35 | DMSO:EtOH 80:20 | 100% DMSO |
| Peak Stress (MPa) | 3.3 ± 0.2 | 4.06 ± 0.32 | 4.6 ± 0.3 | 8.8 ± 0.6 |
| Modulus of Elasticity (MPa) | 56.3 ± 8.9 | 61.4 ± 21.2 | 73.6 ± 12.5 | 59.3 ± 8.5 |

Example 8: Electrospinning of Pure Collagen Fibers

Electrospun collagen scaffolds were collected using a high-speed drum with a surface speed of 10 m/s to generate aligned fibers. Type I atelocollagen (Collagen Solutions, San Jose, Calif.) was dissolved at 250 mg/ml in 40% acetic acid in water for 2-4 hours with gentle rocking. The collagen solution was pumped at 0.2-0.5 ml per hour using a syringe pump (NE-4000 Programmable, New Era Pump Systems, Farmingdale, N.Y.) through a 2-inch-long blunt tip 20 G needle. The distance from the needle tip to the collector (grounded wires spaced 25 mm apart for "air gap" electrospinning) was 10 cm and the needle was charged to +18 kV.

Example 9: Pneumatospinning of Pure Collagen Fibers

An Iwata Gravity feed airbrush (Iwata, Japan) was modified to produce pneumatospun collagen fibers (FIG. 3A). An air pressure of 60 psi (pounds per square inch) was used, and the inner needle of the airbrush was withdrawn approximately 1 mm from the end of the solution emitter to prevent clogging from viscous collagen solution. Up to 500 mg/ml of clinical grade type I atelocollagen (Collagen Solutions, San Jose, Calif.) was dissolved for 2-4 hours in 20-50 vol. % 40% acetic acid (Sigma-Aldrich, St. Louise, Mo.) in water by shaking. The solutions were then tested for the ability to form fibers by pneumatospinning.

Collagen fibers were collected on either static grid (2.5 cm squares of a common 50 ml Eppendorf test tube rack) or were sprayed into a custom rotating tube to collect aligned scaffolds. In the custom engineered rotating tube design, several pairs of perpendicular rods were inserted through a tube to catch the passing fibers while the airflow aligned them in the direction of flow (illustrated in FIG. 3C). The rotating collector tube had 2 1/16" OD parallel stainless steel rods spaced 2.5" apart were placed through the center of a 2" ID PVC tube. These parallel rods were placed in a rifled pattern down the length of the 30" tube at 30 degree increments. The rods acted to catch fibers as they passed through the tube and align them in the direction of flow. The parallel rods were connected to each other by a thin piece of nylon which allowed them to be removed from the side of the tube. The tube was rotated with a simple DC motor and several idler rollers at 10-20 degrees per second. Rotating the tube allowed for even fiber collection, with the airbrush held at approximately 45° C. with respect to the tube inlet. Fibers were collected for 5 minutes of pneumatospinning and used in subsequent examples after storage in a desiccator containing a Bel-Art Scienceware reusable cartridge to ensure dryness.

Pneumatospinning from acetic acid solutions with 20-25 wt. % (for example, as in 450 mg/ml or 500 mg/ml) type I atelocollagen yielded few fibers. Solutions with 45-50% collagen produced fibers, yet the solutions were poorly solubilized, very viscous, and resulted in discontinuous fiber production during pneumatospinning (Table 4). The 40% collagen in 40% acetic acid (aq.) was found to optimally produce a continuous spray of collagen fibers and generate robust sheets of collagen with a static collector (FIG. 3B) that was densely coated with fibers by 5 minutes of spraying, thus these parameters were used for all subsequent experiments in Examples 3-5. The resulting collected scaffolds weighed 45-50% of the starting material (total milligrams of collagen dissolved before pneumatospinning). Pneumatospun scaffolds were collected at around a 32× increased rate relative to electrospinning from acetic acid (Table 5), such as described in U.S. Provisional Application 62/707, 159, incorporated herein by reference. Faster deposition rates of pneumatospun fibers was achievable at higher compressor pressures but with decreased collection efficiency.

TABLE 4

Collagen Concentration in Acetic Acid Test Matrix for Pneumatospinning

| Collagen Concentration | Produced Fibers |
| --- | --- |
| 150 mg/mL | No |
| 200 mg/mL | No |
| 250 mg/mL | Yes |
| 300 mg/mL | Yes |
| 400 mg/mL | Yes |
| 450 mg/mL | Yes |
| 500 mg/mL | No |

TABLE 5

Collagen Fiber Manufacturing Rate

| Output | Electrospinning | Pneumatospinning |
| --- | --- | --- |
| Deposition Rate | 0.0625 g/hr | 2 g/hr |
| Collection Efficiency | 52% | 23% |

Figure 8:
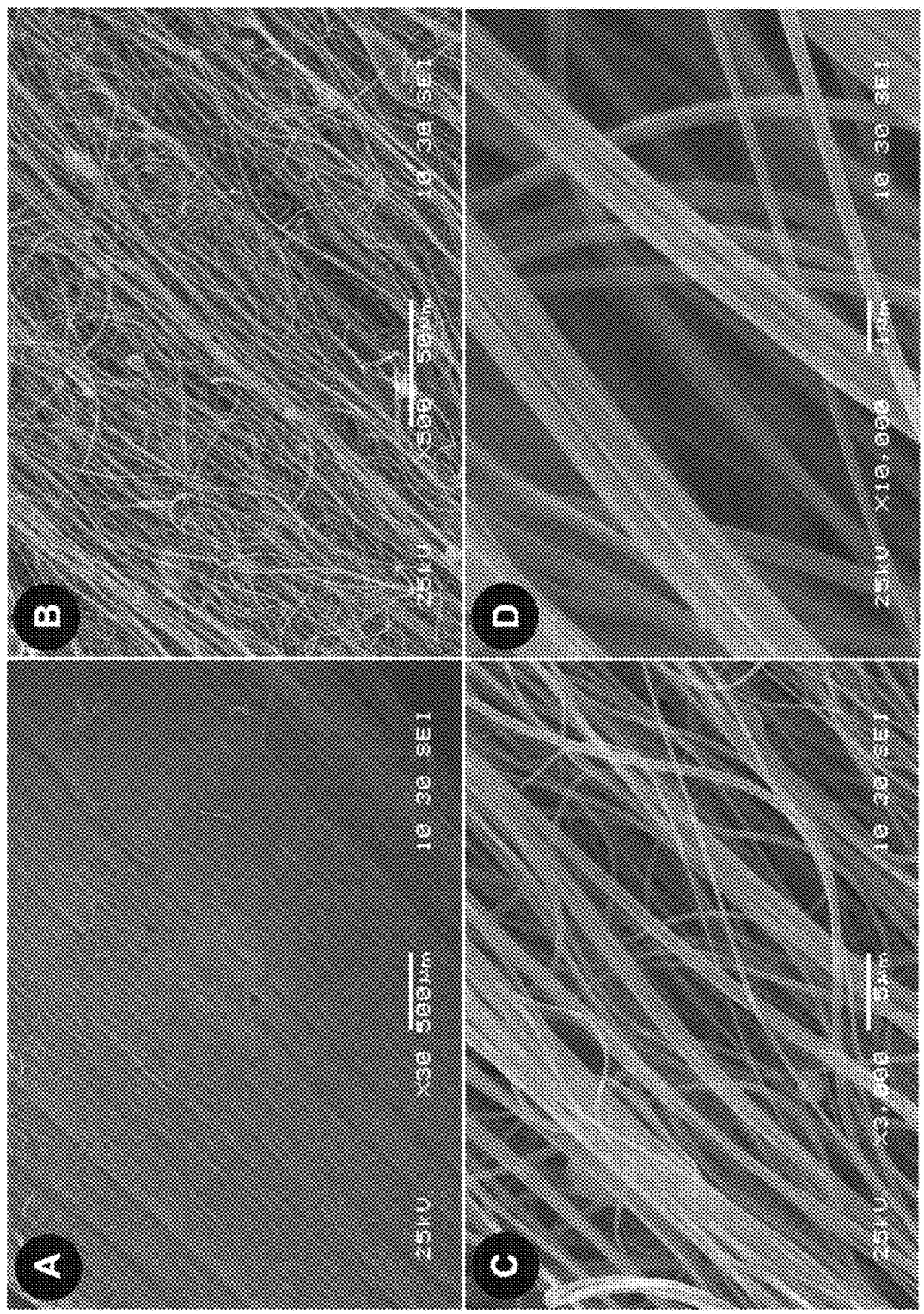
FIGS. 8A-8D show scanning electron microscopy (SEM) of aligned pneumatospun collagen at 30x× (FIG. 8A), 500× (FIG. 8B), 3,000× (FIG. 8C) and 10,000× (FIG. 8D) magnification.
Figure 9:
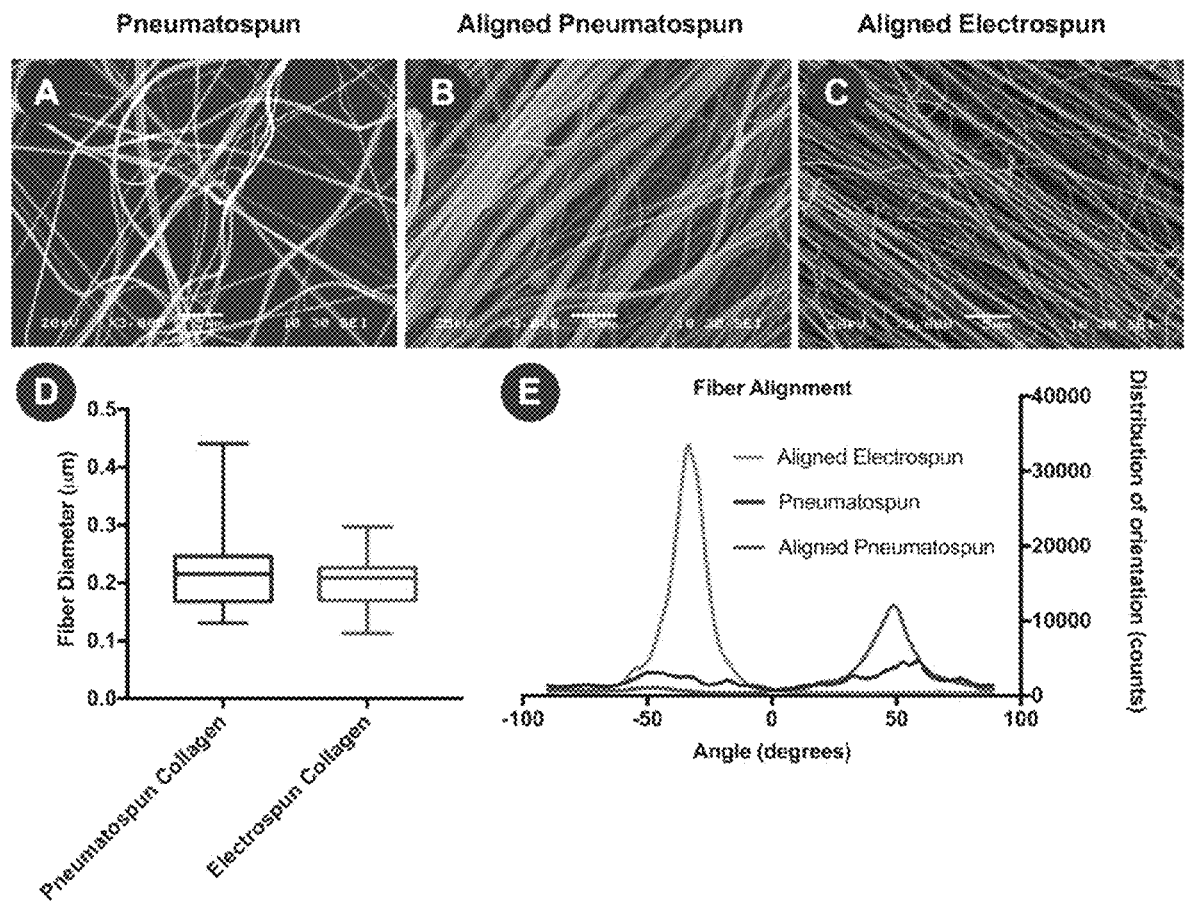
FIGS. 9A-9C show a comparison of aligned collagen fibers. Scanning electron microscopy revealed the potential for generating isotropic and anisotropic collagen fibers by pneumatospinning (FIG. 9A, FIG. 9B), as compared to aligned electrospun collagen generated using electrospinning (FIG. 9C). Although a wider range of fiber sizes were produced via pneumatospinning, both pneumatospinning and electrospinning produced fibers with 200 nm average diameter (FIG. 9D). Fiber alignment quantified using ImageJ showed a greater degree of alignment in electrospun compared to pneumatospun fibers (FIG. 9E).

Collagen fibers (40% acetic acid (aq.), 300 mg/ml atelocollagen) pneumatospun in the rotating tube collection apparatus (FIG. 3C) designed to impart a higher degree of anisotropy to the collected fibers showed a generally aligned array of fibers under SEM (FIG. 8). Orientation J (Image) plugin for NIH shareware, Bethesda, Md.) quantified the overall significant improvement in fiber alignment in pneumatospinning in the rotating collection tube relative to collecting pneumatospun collagen on a static grid (FIGS. 9A and 9B). However, electrospun collagen microfibrous scaffolds consistently demonstrated a significantly higher degree of alignment (p<0.05) than that of the pneumatospun scaffolds (FIG. 9C). The average fiber diameter of pneumatospun relative to electrospun collagen from acetic acid was 0.224±0.051 μm, whereas electrospun collagen had an average fiber diameter of 0.201±0.047 μm (FIG. 9D). Fiber alignment is shown in FIG. 9E.

Example 10: Stability and Mechanical Properties of Pneumatospun Collagen

Pneumatospun atelocollagen was not stable in aqueous media without crosslinking, forming a tacky, gel-like film when hydrated, in contrast to complete dissolution of uncrosslinked electrospun fibers placed in aqueous media. To stabilize the electrospun and pneumatospun collagen matrices (Examples 8 and 9, above) for use in aqueous media, which are otherwise soluble (electrospun) or gel (pneumatospun) when hydrated, genipin was used as a crosslinker. Genipin was chosen for its established low toxicity and existing use in clinically approved medical devices.

A protocol by Mekhail et al. was followed to crosslink both electrospun and pneumatospun aligned type I collagen, as described, for example, in "Genipin-cross-linked electrospun collagen fibers," J Biomater Sci Polym Ed. 2011; 22(17):2241-59. doi: 10.1163/092050610X538209. A solution of 0.03 M genipin (Sigma-Aldrich) in 97% Ethanol (Sigma-Aldrich) was used to crosslink pneumatospun and electrospun scaffolds. Pneumatospun samples were given a short, even twist to improve fiber packing for crosslinking. During crosslinking, samples were clamped to hold tension on the fibers and prevent shrinkage and folding upon itself during the 7-day and incubation period at 37° C. The genipin-ethanol bath was checked every day to ensure the graft remained covered in crosslinking solution. Genipin crosslinked scaffolds were washed 20 times with Phosphate-Buffered Saline (PBS) (Cellgro, Manassas, Va.) to wash away residual, unreacted genipin, producing deep blue scaffolds.

Figure 10:
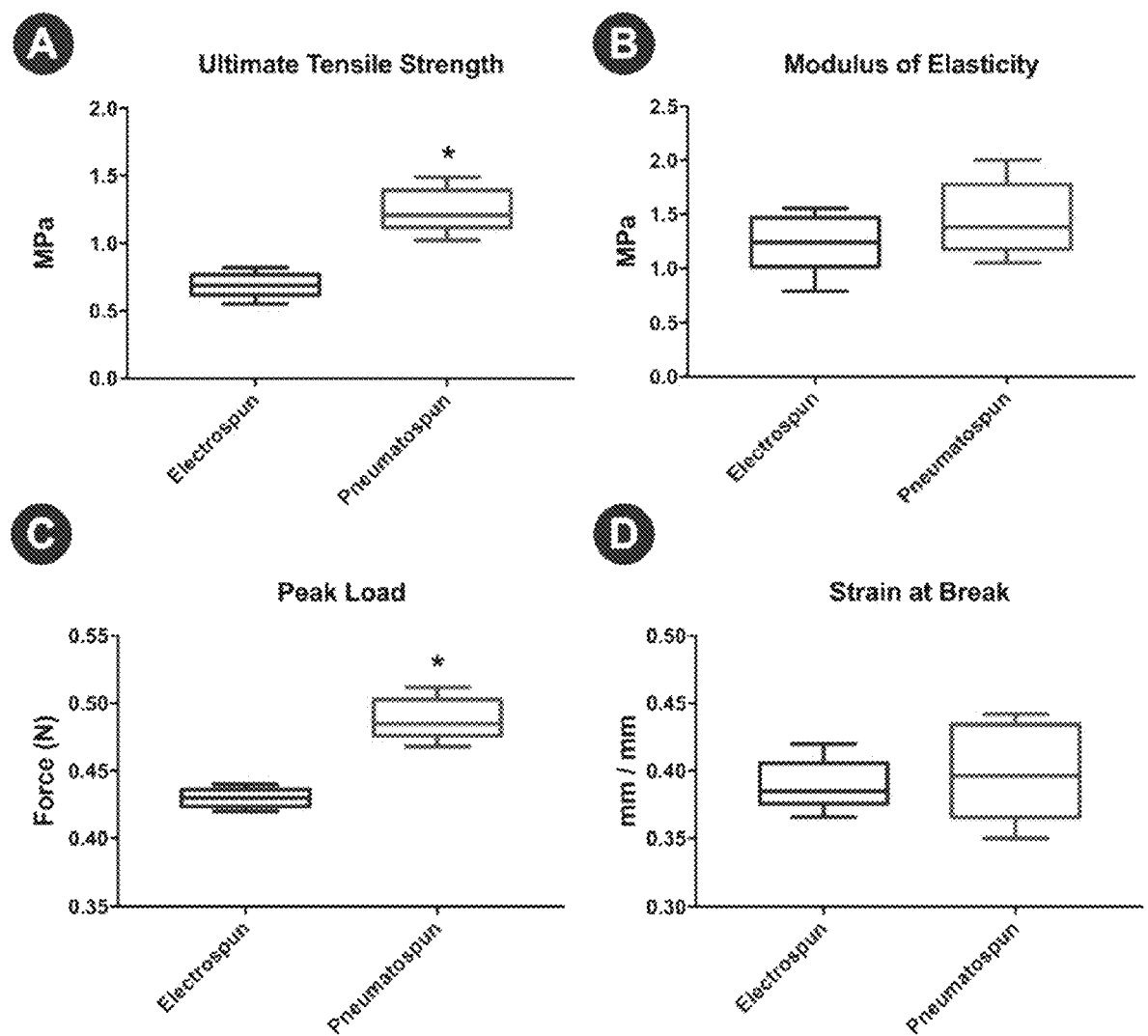
FIG. 10 shows material properties of pneumatospun and electrospun collagen. Genipin crosslinked collagen manufactured by electrospinning and pneumatospinning methods were mechanically tested and compared (n=6). Pneumatospun collagen surprisingly had a significantly higher average tensile strength and peak load compared to the electrospun group (* indicates $p<0.05$), with no statistical difference in the modulus or strain at break found between the two tested groups.

Despite lesser alignment of the fibers relative to electrospun collagen scaffolds (FIG. 9E), pneumatospun collagen from an acetic solvent then crosslinked with genipin (tested hydrated for 1 hour in DMEM) were significantly stronger, at 1.23 MPa±0.11, compared to electrospun scaffolds (FIGS. 10A, C).

There was no significant difference in modulus of elasticity or strain between the groups (pneumatospun collagen at 1.45 MPa±0.34) (FIGS. 10B, D). Pneumatospun collagen scaffolds crosslinking with genipin remained intact for at least 30 days submerged in DMEM at 37° C., left loose (un-restrained), was morphologically altered with an apparent constriction and coiling of the fibers into spheres on the previously fibrous graft.

Example 11: Chemical and Structural Characterization of Electrospun and Pneumatospun Collagen FTIR analyses between the collagen feedstock (unprocessed, freeze dried), electrospun and pneumatospun collagen (Examples 1 and 2, above) showed no shifts in the carboxyl and three amide bonds that are characteristic of type I collagen, indicating integrity of the primary and secondary structure. Circular dichroism analyses showed comparatively little change in pneumatospun collagen relative to the feedstock collagen, suggesting the pneumatospinning process does not denature the protein, preserving the native triple helical structure. SDS-PAGE further confirmed the presence of alpha, beta and gamma chains of collagen present in unprocessed, pneumatospun and electrospun collagen fibers.

Example 12: Cell Viability of ASCs Grown on Electrospun and Pneumatospun Collagen Scaffolds Tissue culture 96 well-plates were coated with 200 μL of 7% poly(2-hydroxyethyl methacrylate) (PHEMA) (Sigma-Aldrich) to prevent cells from attaching to cell culture vessels. Six-millimeter diameter scaffold disks from genipin crosslinked pneumatospun and electrospun collagen (Examples 7 and 8, above) were cut from the scaffold sheets using a tissue biopsy punch. The samples were then disinfected by soaking in 70% isopropanol for 30 minutes, followed by three ten-minute washes in PBS. One scaffold disk was used per well. Human adipose-derived stem cells (ASCs) (ZenBio, Research Triangle Park, N.C.) were mixed and suspended in DMEM. These cells were seeded at a density of $5\times10^4$ cells/well on both the electrospun and pneumatospun scaffolds. Cell viability on collagen-coated wells of a 96-well plate was used as a positive control. Wells were assessed after days 1, 4, and 7 using the alamarBlue™ (BioRad, Hercules, Calif.) viability assay.

After 7 days of culture, the cell-seeded electrospun and pneumatospun scaffolds were fixed and stained to assess cell morphology and attachment. One set of the samples (n=2) was fixed in 4% paraformaldehyde (Thermo Fischer Scientific, Hampton, N.H.) and stained for nuclei and actin filaments using DAPI (Vector Laboratories, Burlingame, Calif.) and Alexa Fluor® 594 phalloidin (Thermo Fischer Scientific), respectively. These stained samples were imaged using confocal microscopy (ZEISS Axio Observer Z1 Inverted Motorized Microscope, Oberkochen, Germany).

A second set of samples (n=2) was fixed in 2% glutaraldehyde (Electron Microscopy Sciences, Hatfield, Pa.) and stained with osmium tetroxide (Electron Microscopy Sciences, Hatfield, Pa.) to image cell morphology on the collagen scaffolds.

Figure 11:
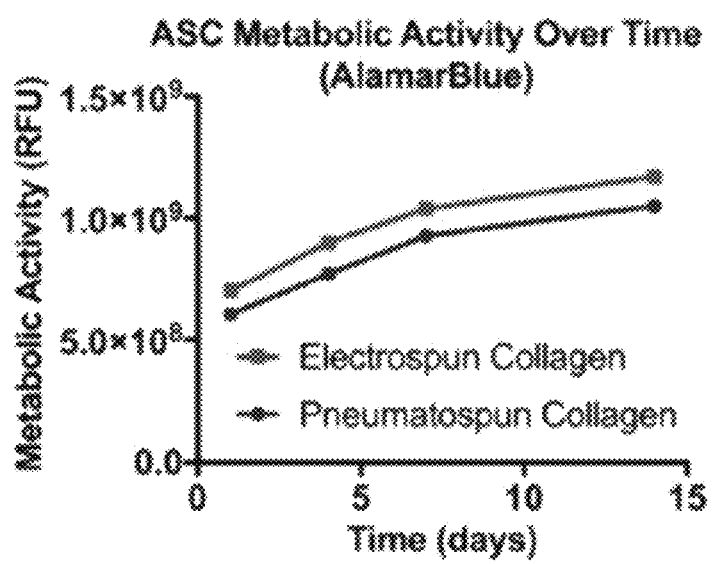
FIG. 11 shows ASC metabolic activity over time (AlamarBlue). ASCs seeded on genipin-crosslinked electrospun and pneumatospun scaffolds at $5\times10^4$ cells/$cm^2$ were incubated for two weeks in cell culture media at 37° C. Increasing metabolic activity over time shows cytocompatibility of both matrices.

The alamarBlue™ assay performed to assess the metabolic activity of ASCs grown on pneumatospun scaffolds using acetic acid and electrospun scaffolds using DMSO, with metabolic activity quantified as increasing over time (FIG. 11), indicated cellular proliferation and viability over 14 days in culture. Confocal imaging of ASCs grown for two weeks on pneumatospun and electrospun collagen cross-linked with genipin reveal that cells were present throughout the matrices. A confluent layer of cells was found atop both groups by SEM, collectively indicating strong cell attachment and cytocompatibility for pneumatospun collagen.

The pneumatospun biopolymers are shown to be stable in culture conditions for a month, yet with an apparent alteration of the fiber morphology and overall graft topography to a condensed and coiled appearance. This may be partially related to the constriction of material over time as the grafts were not held under tension, along with the crosslinking driving this apparent fiber constriction and coiling. Other crosslinkers, such as glyceraldehyde and glutaraldehyde, did not exhibit this change in morphology, suggesting a genipin-related effect on pneumatospun collagen. Despite morphological changes to the material, cell metabolic activity and related cell viability was high on pneumatospun fibers though at least 2 weeks of culture.

Example 13: Pneumatospinning Collagen and PDLLA Blended Scaffolds from DMSO

To assess if collagen could be combined with a biopolymer to produce a blended biomaterial via pneumatospinning, collagen was dissolved in DMSO-based solvent system along with PDLLA in a 30:70 ratio as empirically determined for optimal fiber production. Telocollagen (Collagen Solutions, San Jose, Calif.) was dissolved with poly-d,l-lactide (Polysciences, Warrington, Pa.) in dimethylsulfoxide (DMSO, Sigma-Aldrich, St. Louis, Mo.), or DMSO and absolute ethanol (Sigma-Aldrich) at 150 mg/mL and collected on a static grid as described in Example 9, above. While pneumatospinning of collagen alone from DMSO was not achieved at the tested concentration, PDLLA alone and collagen:PDLLA blends were able to form produce scaffolds by pneumatospinning from DMSO alone and from DMSO:ethanol co-solvent system (Table 6). Collagen:PDLA ratios ranging from about 10:90 to 50:50 may be used to prepare pneumatospun fibers according to the invention. FTIR analyses of the pneumatospun collagen:PDLLA confirmed presence of both biomaterials in the collected scaffold. The ability to blend collagen with a biopolymer, such as poly- d,l-lactic acid here, presents further potential applications of a pneumatospinning method according to the invention.

TABLE 6

| Solvent Compatibility for PDLLA:Collagen Pneumatospinning from DMSO | | | |
|---|---|---|---|
| Solvent and Volume Ratio | Telocollagen Only | PDLLA Only | Telocollagen and PDLLA |
| DMSO (100%) | No | Yes | Yes |
| DMSO:EtOH (80:20) | No | Yes | Yes |
| DMSO:EtOH (65:35) | No | Yes | Yes |

Example 14: Pneumatospun Fibers Using Telocollagen Dissolved in pH3 Buffer

Pneumatopsun teleocollagen fibers were produced using the following procedure:
Preparation of pH 3 buffer:
i. Dissolve 1.2 grams of sodium acetate (final 292 mM) into 22.5 ml Acetic acid (47%) and 27.5 ml MilliQ Water. Adjust pH to 3 using Acetic Acid.
Prepared 10 ml of 300 mg/ml of Telocollagen (cut into pieces) in the pH 3 buffer in a scintillation vial 24 h prior to airbrushing. Left overnight on a rocker (speed 5; Tilt 10) after briefly vortexing @ 400 rpm for 1 h @ RT. After 24 h, the telocollagen solution was viscous but the telocollagen had completely dissolved.

On the day of pneumatospinning, the following setup was made,
ii. The airbrush was cleaned using water, acetic acid, water and then ethanol before use.
iii. The airbrush needle was pulled out so 6 cm of it was exposed at the end of the airbrush.
iv. Set the drum to a medium speed and the air compressor at 60 psi
v. Airbrush was held 24 inches away from the drum in a box setup. A cardboard ramp was set up so the liquid would settle on the ramp and so the fibers could go off the ramp and collect on the rotating drum.
vi. Fibers collected on the drum at first but then started to avoid the drum and formed in the surrounding leading to significant loss.
vii. The pressure was then lowered to 40 psi and the drum speed was changed to lower speeds.
viii. The fibers began to form on the drum again, however, there was significant accumulation of long fibers around the drum in the box.

Around 9 ml of solution was airbrushed in 1.5 h. However, more than 40% (approximate estimate based on accumulation on the drum) of the fibers were lost as the air flow to dry the fibers within the box was sucking up a significant amount of fibers.

The fibers on the drum were air dried for 24 h followed by 24 h in the chemical fume hood.

On imaging the fibers, they appeared wet and hence they were vacuum dried for 3 h when on the drum.

Example 15: Cell Attachment, Proliferation and Infiltration

Aligned electrospun scaffolds were produced by blending telocollagen and PDL45 at a ratio of 30:70, respectively and dissolving in 100% DMSO at a final concentration of 100 mg/ml. This polymer blend was electrospun onto a wire wheel collector in a vertical electrospinning setup.

One set of the scaffolds was restrained in aluminum frames and annealed at 65° C. for 18 hours to promote further fiber alignment and improved mechanical stability. All scaffolds were cut into 10×30 mm strips and electron beam (E-beam) sterilized prior to cell experimentation.

To assess human tenocyte cell attachment, one set of each as-spun or annealed scaffolds (n=3) were placed in grips and held under static tension to prevent shrinkage and promote further fiber alignment (these scaffolds are referred to as 'gripped' scaffolds). The available cell seeding area of these scaffolds in the grips is 10×10 mm. Second sets of each as-spun or annealed scaffolds (n=3) were cut into 10×10 mm pieces to match the available seeding area of the gripped scaffolds. These samples were placed in ultra-low cell binding culture plates without tension (These scaffolds are referred to as 'loose' scaffolds). Human tenocytes were suspended in serum-free media, seeded at a density of $1 \times 10^5$ cells/scaffold and remained in culture for 30 and 60 minutes. Cell attachment on collagen-coated wells was used as a positive control. At each time point the scaffolds were removed from the wells and washed 4 times by dipping in separate media-containing wells to remove the non-attached cells. The number of non-attached cells suspended in each well was counted and the percentage of attached cells on each scaffold was determined based on the total number of cells seeded.

To assess human tenocyte cell proliferation one set of each as-spun and annealed gripped scaffolds (n=6) and one set of each as-spun and annealed loose scaffolds (n=3) were seeded with $25 \times 10^3$ cells/scaffold. Cellular proliferation was assessed after 1, 7 and 14 days in culture. The alamarBlue™ metabolic activity assay is a standard method to test compatibility of device with an intended cell type. Healthy and metabolically active cells will metabolize resazurin from alamarBlue. The metabolism of resazurin (blue in color) reduces it to resorufin (red in color), allowing fluorescent monitoring of metabolic activity in the cell media over time. Both metabolite and the byproduct are non-toxic. Alamar-Blue fluorescence level is directly proportional to the number of viable cells as it measures the metabolic activity of live cells.

Cell infiltration was assessed over a 14-day time frame. One set of each as-spun and annealed gripped scaffolds (n=3) and one set of each as-spun and annealed loose scaffolds (n=3) were seeded with $1 \times 10^5$ cells/scaffold. Cellular infiltration was assessed after 1, 7 and 14 days in culture. Cells were stained with DAPI nucleic stain and cellular infiltration was measured by confocal microscopy. Five fields of view per each scaffold were investigated. At each field of view, multiple 5 μm thick z-scan slices were captured and the total depth of cell infiltration was calculated based on the number of cell containing slices captured. The total depth was averaged between the five fields of view.

Statistics:

All parameters are expressed as mean±standard error of the mean (S.E.M). Two-way analysis of variance (ANOVA) followed by the post-hoc Tukey's Multiple Comparison Test was used to assess the differences in cell attachment, proliferation and infiltration. A priori, p values below 0.05 were defined as significant.

Annealed and as-spun scaffolds (gripped and loose) were seeded with human tenocytes to assess the ability of these scaffolds to support cell attachment. After 30 and 60 minutes in culture, all scaffolds showed greater than 50% and 90% cell attachment, respectively. There were no significant differences in cell attachment between all conditions tested after 60 minutes (p>0.05). Additionally, the proliferation of human tenocytes was assessed on gripped and loose, annealed and as-spun scaffolds after 1, 7 and 14 days in culture. All scaffolds that were tested supported cell viability and proliferation. It was shown that a significantly higher number of metabolically active cells were present on all scaffolds after 7 and 14 days in culture (p<0.05). The smaller number of cells within the loose scaffolds is partially due to spillage of a small amount of cell suspension off the scaffolds during cell seeding and mainly due to reduced available growth area as a result of scaffold shrinkage.

Assessment of cellular infiltration determined that none of the scaffolds promoted significant cell infiltration over a 14-day time period. However, after 7 days in culture gripped as-spun scaffolds showed significantly deeper cell infiltration compared to loose, as-spun scaffolds (p<0.05). Additionally, after 14 days in culture gripped annealed scaffolds supported significantly deeper cell infiltration than loose as-spun scaffolds (p<0.05).

Example 16: Physical Properties of Telocollagen-PDL45 Scaffolds in Culture

Figure 12:
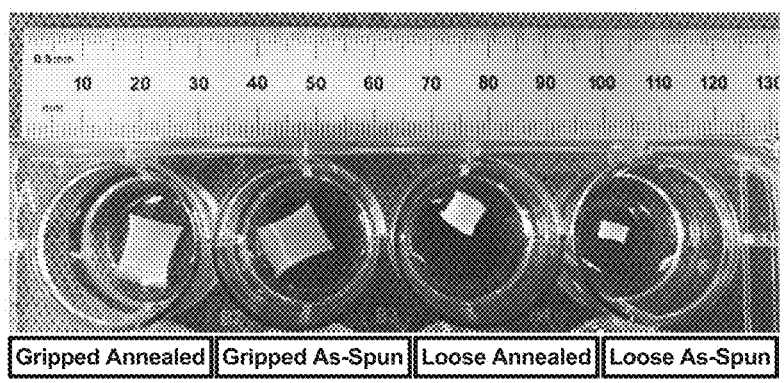
FIG. 12 shows shrinkage of biopolymer sheets that are not annealed or restrained.
Figure 13:
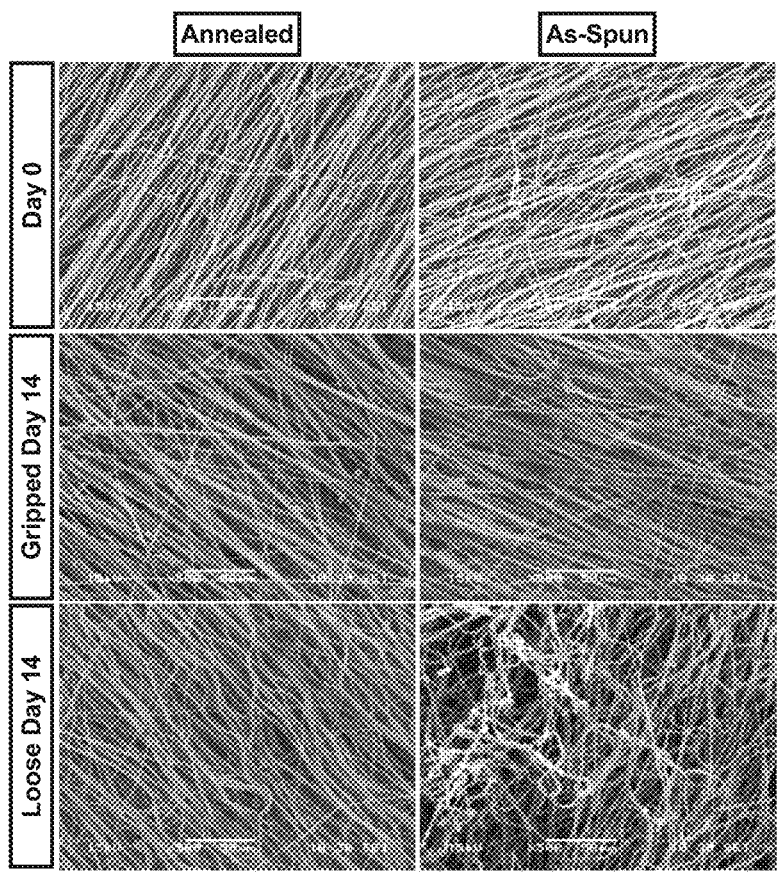
FIG. 13 shows scanning electron microscopy (SEM) images of annealed and as-spun (gripped and loose) scaffolds after 14 days in culture.
Figure 14:
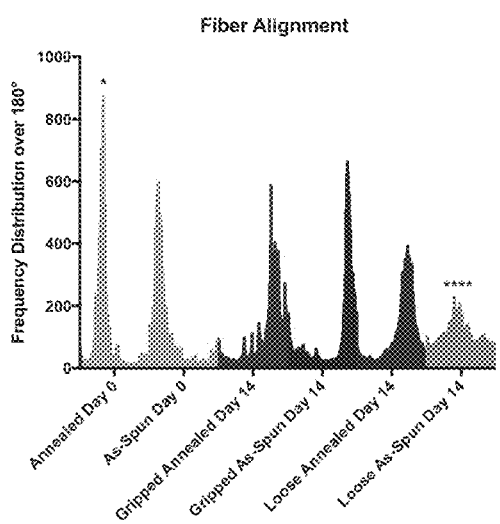
FIG. 14 shows fiber alignment at days 0 and 14 for biopolymer scaffolds with or without annealing or restraining.
Figure 15:
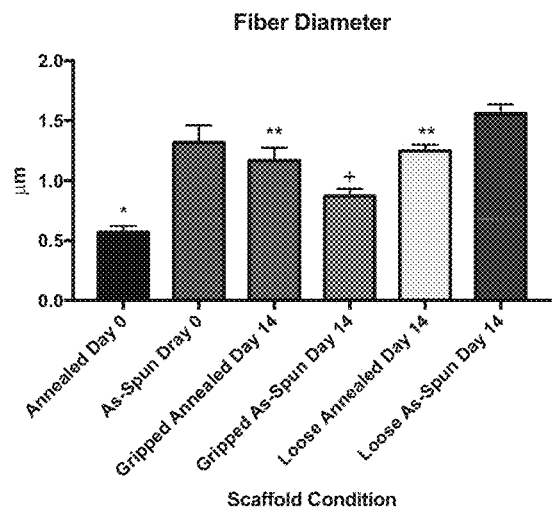
FIG. 15 shows fiber diameters at days 0 and 14 for biopolymer scaffolds with or without annealing or restraining.

Annealed and as-spun telocollagen-PDL45 electrospun scaffolds were produced and gripped as described above. FIG. 12 shows shrinkage of biopolymer sheets that are not annealed or restrained. After 14 days in culture the annealed and as-spun (gripped and loose) scaffolds were imaged through scanning electron microscopy (SEM) (FIG. 13). Fiber alignment and fiber diameters were measured using ImageJ software (available at imagej.nih.gov/ij/). These measurements were compared with fiber alignment and diameters of loose scaffolds at day 0 after a 30-minute soak in phosphate buffered saline (PBS) (FIGS. 14 and 15). Fiber alignment was measured using the 'Directionality' function of ImageJ. This function captures the direction of the fibers and plots a histogram showing the number of occurrences that a fiber has laid within a certain angle. Therefore, a narrower and higher histogram represents more fibers within a certain direction.

Statistics:

All parameters are expressed as mean±S.E.M. Unpaired nonparametric Kolmogorov-Smirnov t test was used to assess the differences in frequency distribution of fiber alignment. One-way analysis of variance (ANOVA) followed by the post-hoc Tukey's Multiple Comparison Test was used to assess the differences in fiber diameters. A priori, p values below 0.05 were defined as significant.

It is shown that annealing under static tension results in further fiber alignment and a decrease in fiber diameter as a result of a scaffold's tendency to shrink. These physical changes are demonstrated by the significant differences in fiber alignment and diameter between annealed and as-spun scaffolds at day 0 (FIGS. 14 and 15). Telocollagen-PDL45 scaffolds shrink in media at 37° C. However, through annealing or gripping these scaffolds under static tension in culture, scaffold shrinkage and loss of fiber alignment was substantially reduced. As depicted in FIG. 12, it is evident that after 14 days in culture the gripped scaffolds retain their initial size whereas the annealed loose scaffolds only retain about 60% of initial size and the loose as-spun scaffolds shrink to less than 25% of their initial size. Additionally, SEM images depicted in FIG. 13 demonstrate that both annealed and as-spun gripped scaffolds remain highly aligned while both annealed and as-spun loose scaffolds lose their fiber alignment in culture. ImageJ fiber alignment analysis of the SEM images revealed that annealed scaffolds at day 0 show significantly higher degree of fiber alignment than all other scaffolds tested (p<0.05). It is shown that gripped scaffolds retain their fiber alignment while there is loss of fiber alignment within loose scaffolds. The degree of fiber alignment within as-spun loose scaffolds was significantly reduced compared to all other scaffolds tested (p<0.0001). It is apparent that this loss of fiber alignment is due to the shrinkage observed within loose as-spun scaffolds.

Analysis of fiber diameters suggest that annealed scaffolds at day 0 exhibited significantly smaller fiber diameters than all other scaffolds tested except gripped as-spun day 14 scaffolds (p<0.05). This decrease in fiber diameter is due to the tendency of restrained scaffolds to shrink under heat treatment. Both gripped and loose annealed scaffolds experienced fiber swelling shown by the significant increase of their fiber diameter (p<0.0001). The significant decrease in fiber diameter of gripped as-spun scaffolds compared to as-spun day 0 suggests that restraining as-spun scaffolds in culture may induce the same physical effects as annealing. There were no significant differences in the fiber diameter of the loose as-spun fibers after 14 days in culture (FIG. 15).

Example 17: Cellular Morphology and Elongation on Telocollagen-PDL45 Electrospun Scaffolds Annealed and as-spun scaffolds were prepared as described above. Both gripped and loose scaffolds were seeded with $1 \times 10^5$ human tenocytes per scaffold and remained in culture for up to 14 days. To visualize cell morphology and elongation all the scaffolds cultured with human tenocytes were fixed in 4% paraformaldehyde and stained for nuclei and actin filaments using DAPI and Alexa Fluor® 594 phalloidin, respectively. The stained samples were imaged using confocal microscopy. Percentage of cell elongation was determined based on the average calculated nuclei aspect ratio by measuring the length and width of twenty cell nuclei. Additionally, the degree of cell alignment was determined by measuring the angle of twenty elongated cells in the direction of elongation over 180° and the frequency distribution was presented at every 2°. Both measurements were performed using confocal images taken at 40× magnification.

The results demonstrate that human tendon cells had a higher percent of elongation within the gripped scaffolds as compared to the loose scaffolds. This is due to higher degree of fiber alignment within the gripped scaffolds as they retain their shape whereas the loose scaffolds lose their fiber alignment due to shrinkage and swelling. The direction of actin filaments (red) demonstrates cell elongation on the gripped annealed and gripped as-spun scaffolds along the direction of the fibers. The random morphology of actin filaments in the cells on the loose scaffolds demonstrates the loss of fiber alignment within these scaffolds. This random morphology is confirmed by the SEM images of the fibers shown in Example 16, FIG. 13. Cellular spreading and percent elongation were assessed by cell aspect ratio measurements. Both annealed and as-spun gripped scaffolds supported significantly higher percent cell elongation when compared to their loose counterparts (p<0.0001 and p<0.01). Additionally, the frequency distribution of cellular directionality revealed a higher degree of cellular alignment within the gripped scaffolds.

Example 18: Assessment of Heat Treated Tellocollagen-PDL45 Electrospun Scaffolds Application of heat to enhance stability and structure of electrospun fibers:
1. Aligned electrospun sheets of feedstock were produced by dissolving telocollagen-PDL45 (30:70) in 100% DMSO at 100 mg/ml.
2. Scaffolds were post processed by:
    a. Annealing at 65° C. for 18 hours
    b. Annealing at 65° C. under vacuum for 18 hours
    c. Drawing to 30% strain at 85° C.
3. Scaffolds were assessed for:
    a. Impact of temperature and vacuum on electrospun scaffolds
    b. Changes in biochemical and mechanical properties as a result of heat treatment using XRD, Fourier Transform Infrared Spectroscopy (FTIR), DSC, Sodium Dodecyl Sulfate Polyacrylamide Gel Electrophoresis (SDS-PAGE), SEM and uniaxial tensile testing.

Statistics:

All parameters are expressed as mean±S.E.M. Unpaired nonparametric Kolmogorov-Smirnov t test was used to assess the differences in frequency distribution of fiber alignment. Ordinary One-way analysis of variance (ANOVA) followed by the post-hoc Tukey's Multiple Comparison Test was used to assess the differences in peak stress, modulus of elasticity, % strain at break and peak load. A priori, p values<0.05 were defined as significant.

The mechanical properties of as-spun and heat-treated scaffolds were assessed to evaluate impact of temperature and vacuum on fibers. Mechanical testing indicated that all treatments significantly increased peak stress of scaffolds when compared to as-spun control group (p<0.05). Among treated groups, scaffolds drawn at 85° C. showed significantly higher peak stress than scaffolds annealed at 65° C. (p<0.05). The heat-treated groups exhibited significantly higher modulus of elasticity than the as-spun control group, however, the scaffolds drawn at 85° C. exhibited lower modulus of elasticity than both annealed groups (p<0.01). Although, peak stress and modulus of elasticity were affected by heat treatment there were no significant differences observed in their peak load. Both annealing conditions improved strain at break significantly (p<0.05). Scaffolds annealed at 65° C. without vacuum exhibited the highest % strain at break (p<0.05). These results indicate heat treatment impacts the structure of the fibers and promotes increased peak stress, modulus of elasticity and % strain at break. This could be due to changes in degree of fiber and molecular alignment.

To determine the impact of heat treatment on the restrained or drawn scaffolds, SEM images were taken and fiber alignment was analyzed using the 'Directionality' function of ImageJ, as described in Example 16. The results show that fiber alignment was significantly improved within scaffolds drawn at 85° C. or annealed at 65° C. (p<0.05). Although the drawn electrospun scaffolds under 85° C. exhibit a high degree of fiber alignment, the corresponding SEM image shows that some of the fibers were broken, therefore, this method may not be ideal for tissue regeneration.

Additionally, the impact of post-processing on the crystallinity of polymers was assessed. Telocollagen and PDL45 fiber crystallinity was evaluated using XRD. The results show that all groups have similar intensity and the peaks overlap indicating that heat treatment did not have an impact on polymer crystallinity. Scaffolds treated at 65° C. under vacuum had a lower peak intensity and a slight shift to the right on the 2θ axis.

The effect of heat on these scaffolds was also analyzed by FTIR. These results confirmed the presence of collagen within the heat-treated groups by presence of amide I (~1650 cm$^{-1}$), amide II (~1560 cm$^{-1}$), amide A (~3285 cm$^{-1}$) and amide B (~2917 cm$^{-1}$) bonds. The amide III (~1245 cm$^{-1}$) bond could not be easily distinguished as PDL45 has the same FTIR fingerprint as collagen within this area. Because the peak is slightly shifted from the pure collagen, we cannot fully determine if this peak is from the collagen or if it is due to the peak from PDL45. If amide III from collagen is present but the peaks have shifted, it indicates that the state of the bond has changed. However, FTIR shows presence of amides I, II, A, and B bonds, which confirms collagen presence within all heat-treated groups.

Collagen denaturation of annealed samples was analyzed and compared to collagen starting material and as-spun control groups. The DSC graph shows two peaks for collagen starting material; a broad peak at ~90° C. and a sharp peak at ~200° C. The graph shows as-spun control and annealed groups have shifted to lower temperatures when compared to collagen starting material. Even though collagen thermal denaturation temperature decreased after electrospinning, DSC data suggests that annealing increases denaturation temperature as the peak for the annealed sample is ~58° C. while as-spun control is ~55° C.

Another method used to examine the impact of electrospinning, heat annealing, and vacuum drying on collagen chains is SDS-PAGE. As-spun and heat-treated scaffolds were dissolved in acetic acid or DMSO and run on SDS-PAGE. The distinct bands visible at 238 and 117 kDa confirm the presence of alpha and beta chains, respectively, within electrospun fibers. Moreover, lack of smearing below 117 kDa shows collagen has not broken down due to electrospinning or any post-process treatments.

Example 19: Subcutaneous Implant Cell Quantification

Figure 16:
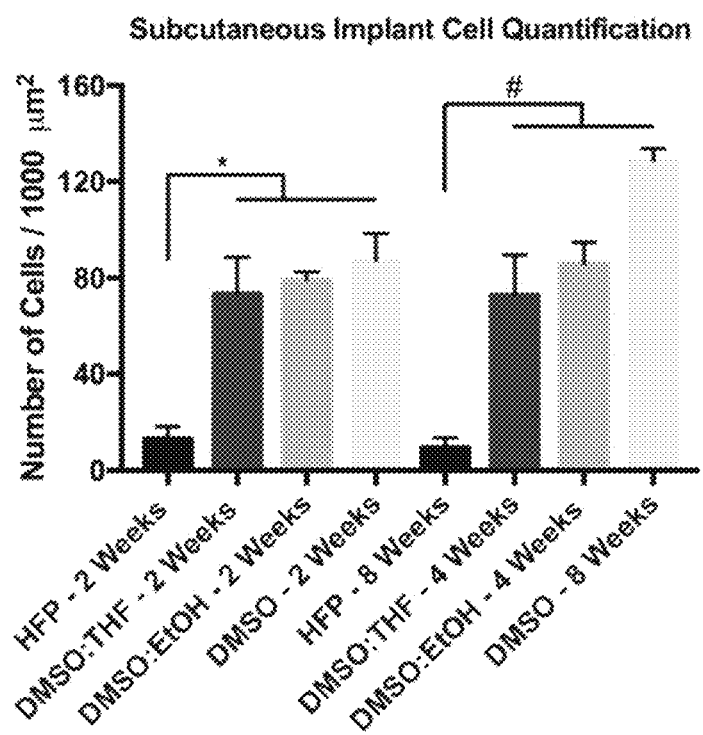
FIG. 16 shows a comparison of subcutaneous implant of scaffolds electrospun out of various solvents to analyze cell infiltration at various time points.

Subcutaneous implant of scaffolds electrospun out of various solvents were compared to analyze cell infiltration at different time points. The result indicates that scaffolds electrospun out of DMSO have significantly higher number of cells when compared to HFP scaffolds at 2 and 8 week time points after implantation (FIG. 16).

Example 20: Determination of Residual DMSO

GC/MS was used to determine residual DMSO in electrospun scaffolds. The grafts that were vacuumed for 2, 4, 6 and 24 hours were compared to grafts that were not vacuumed. The GC/MS analysis on the samples were performed by Mass Spec Lab, CA, USA using an Agilent 7890A GC and data was analyzed using the ChemStation software.

Dimethylacetamide (DMAC) was used as the extraction solvent to recover the DMSO from the scaffolds. Briefly, about 20 mg of the test samples were suspended in 3 mL of DMAC solvent (extraction 1). After heating these at 60° C. with agitation for 24 h, the supernatants were used for GC/MS analysis. Duplicate extracts were prepared for each of the samples (duplicates labeled 1 and 2; see Table 7) as well as 2 injections were run for each duplicate (inj. 1 and inj. 2 in Table 7). A second extraction step (extraction 2) (with the residue of the same sample) was conducted to confirm complete recovery of residual DMSO. Upon running both extracted supernatants (extraction 1 and extraction 2), it was observed that the first extraction was able to extract over 95% of the DMSO. A standard curve for DMSO in DMAC was generated using the integrated area of the most intense ion peak for DMSO as a function of DMSO concentration. The extent of DMSO in the unknown samples was then determined using this standard curve.

Table 7 shows a summary of the results obtained from the GC/MS study on the scaffolds. Data in Table 7 clearly indicates that the amount of DMSO extracted from our samples are significantly below (>1000-fold less) than the acceptable range of 50 mg/dose/day, according to FDA guidelines.

TABLE 7

Summary of results obtained from GC/MS study to determine residual concentrations of DMSO in the scaffolds

| Sample | Run | Mass of Scaffold (gm) | DMSO Peak Area | Amount of DMSO (gm) | % by weight DMSO | Average % by weight DMSO | Standard Deviation |
|---|---|---|---|---|---|---|---|
| No vacuum | inj. 1 | 0.0189 | 10689883 | 0.00033 | 1.770 | 1.74 | 0.033 |
|  | inj. 2 | 0.0189 | 10655792 | 0.00033 | 1.764 |  |  |
|  | inj. 1 | 0.0195 | 10662179 | 0.00033 | 1.710 |  |  |
|  | inj. 2 | 0.0195 | 10654148 | 0.00033 | 1.709 |  |  |
| Vacuum 2 hrs | inj. 1 | 0.0202 | 10805416 | 0.00034 | 1.675 | 1.66 | 0.020 |
|  | inj. 2 | 0.0202 | 10805559 | 0.00034 | 1.675 |  |  |
|  | inj. 1 | 0.0188 | 9960636 | 0.00031 | 1.647 |  |  |
|  | inj. 2 | 0.0188 | 9895768 | 0.00031 | 1.635 |  |  |
| Vacuum 4 hrs | inj. 1 | 0.0209 | 10823608 | 0.00034 | 1.622 | 1.65 | 0.033 |
|  | inj. 2 | 0.0209 | 10834614 | 0.00034 | 1.624 |  |  |
|  | inj. 1 | 0.0192 | 10322380 | 0.00032 | 1.677 |  |  |
|  | inj. 2 | 0.0192 | 10354167 | 0.00032 | 1.683 |  |  |
| Vacuum 6 hrs | inj. 1 | 0.0189 | 10055074 | 0.00031 | 1.656 | 1.66 | 0.009 |
|  | inj. 2 | 0.0189 | 10008145 | 0.00031 | 1.647 |  |  |
|  | inj. 1 | 0.0203 | 10816384 | 0.00034 | 1.669 |  |  |
|  | inj. 2 | 0.0203 | 10756775 | 0.00034 | 1.659 |  |  |
| Vacuum 24 hrs | inj. 1 | 0.0202 | 9723421 | 0.00030 | 1.493 | 1.48 | 0.019 |
|  | inj. 2 | 0.0202 | 9738375 | 0.00030 | 1.496 |  |  |
|  | inj. 1 | 0.0208 | 9794527 | 0.00030 | 1.462 |  |  |
|  | inj. 2 | 0.0208 | 9789379 | 0.00030 | 1.461 |  |  |

REFERENCES

All documents identified in this specification, including the following articles, are incorporated by reference in their entireties.

Addad et al., "Isolation, characterization and biological evaluation of jellyfish collagen for use in biomedical applications," Mar Drugs. 2011; 9(6):967-83. doi: 10.3390/md9060967. Epub 2011 Jun. 7.

Cheng et al., "Isolation, Characterization and Evaluation of Collagen from Jellyfish Rhopilema esculentum Kishinouye for Use in Hemostatic Applications," PLoS One. 2017 Jan. 19; 12(1):e0169731. doi: 10.1371/journal.pone.0169731. eCollection 2017.

Elamparithi, Anuradha, Alan M. Punnoose, and Sarah Kuruvilla, "Electrospun type I collagen matrices preserving native ultrastructure using benign binary solvent for cardiac tissue engineering," Artificial cells, nanomedicine, and biotechnology 44.5 (2016): 1318-1325.

Huanga et al., "A review on polymer nanofibers by electrospinning and their applications in nanocomposites," Composites Science and Technology, 63(15):2223-2253 (2003).

Hochleitner et al., "Melt Electrowriting of Thermoplastic Elastomers," Macromol Rapid Commun. 2018 Apr. 14:e1800055. doi: 10.1002/marc.201800055.

Hochleitner et al., "Melt electrowriting below the critical translation speed to fabricate crimped elastomer scaffolds with non-linear extension behaviour mimicking that of ligaments and tendons," Acta Biomater. 2018 May; 72:110-120. doi:10.1016/j.actbio.2018.03.023. Epub 2018 Mar. 17.

Hrynevich et al., "Dimension-Based Design of Melt Electrowritten Scaffolds," Small. 2018 Apr. 30:e1800232. doi: 10.1002/smll.201800232.

Jacob, Stanley W., and Robert Herschler, "Pharmacology of DMSO," Cryobiology 23.1 (1986): 14-27.

Krishnamoorthi et al., "Isolation and partial characterization of collagen from outer skin of Sepia pharaonis" Biochem Biophys Rep. 2017 Feb. 27; 10:39-45. doi: 10.1016/j.bbrep.2017.02.006. eCollection Middleton et al., "Synthetic biodegradable polymers as orthopedic devices," Biomaterials 21:2334-2346 (2000).

Rudolph et al., "Surface Modification of Biodegradable Polymers towards Better Biocompatibility and Lower Thrombogenicity," http://journals.plos.org/plosone/article?id=10.1371/journal.pone.0142075.

Shekhar et al., "Electrospun Collagen: A Tissue Engineering Scaffold with Unique Functional Properties in a Wide Variety of Applications," Journal of Nanomaterials 2011 Article ID 348268.

Shoseyov et al., US 2012/0273993 entitled "Method of Generating Collagen Fibers."

Siow et al., "Plasma Methods for the Generation of Chemically Reactive Surfaces for Biomolecule Immobilization and Cell Colonization—A Review," http://plasmatechsystems.com/about/pubs/Plasma%20Methods%20for%20Chemically%20Reactive%20Surfaces%20for%20Biomolecule%20-Immobilization.pdf Tham et al., "Surface Modification of Polylactic Acid (PLA) via Alkaline Hydrolysis Degradation," https://www.researchgate.net/profile/Zuratul_Abdul_Hamid/publication/277306838_Sur face_Modification_of_Poly_lactic_acid_PLA_via_Alkaline_Hydrolysis_Degradation/links/556 6afd408aeab77721cbfa7/Surface-Modification-of-Poly-lactic-acid-PLA-via-AlkalineHydrolysis-Degradation.pdf Zagho et al., "Recent Trends in Electrospinning of Polymer Nanofibers and their Applications as Templates for Metal Oxide Nanofibers Preparation," Chapter 1 in "Nanotechnology and Nanomaterials" edited by Haider et al., ISBN 978-953-51-2822-9, Print ISBN 978-953-51-2821-2, Published: Dec. 21, 2016 under CC BY 3.0 license. 26 Continuation Application Zhang, Kuihua, et al., "Electrospun scaffolds from silk fibroin and their cellular compatibility," Journal of Biomedical Materials Research Part A 93.3 (2010): 976-983.

Zhong et al., "Isolation and characterization of collagen from the body wall of sea cucumber Stichopus monotuberculatus," J Food Sci. 2015 April; 80(4):C671-9. doi: 10.1111/1750-3841.12826. Epub 2015 Mar. 21.

The claimed invention is:

1. A method for producing an implantable ligament and tendon repair device comprising the steps of:
   dissolving Type I collagen and a bio-acceptable polymer selected from the group consisting of PDLA, PDLLA, PLGA, and mixtures thereof, in a DMSO solvent system comprising about 40 to 100% by volume of DMSO and about 0 to 60% by volume of a solvent selected from the group consisting of ethanol, tetrahydrofuran and acetic acid to form a biopolymer solution;
   generating biopolymer fibers from the biopolymer solution;
   collecting the biopolymer fibers to form a biopolymer sheet; and
   annealing the biopolymer sheet; and
   wherein the biopolymer fibers comprise about 10 to 35% by weight of Type I collagen and about 65 to 90% by weight of the bio-acceptable polymer; and
   wherein the biopolymer fibers in the biopolymer sheet are not chemically cross-linked.

2. A method of claim 1, wherein the biopolymer fibers further comprise:
   about 20 to 35% by weight of Type I collagen and about 65 to 80% by weight of the bio-acceptable polymer.

3. A method of claim 2, wherein the Type I collagen is selected from the group consisting of atelocollagen, telocollagen, recombinant human collagen and mixtures thereof.

4. A method of claim 3, wherein the biopolymer fibers have an average diameter of 700 nm to 1,500 nm.

5. A method of claim 1, wherein the biopolymer fibers are generated by a technique selected from the group consisting of electrospinning and pneumatospinning.

6. A method of claim 2, wherein the biopolymer fibers further comprise about 27.5 to 32.5% by weight of Type I collagen and about 67.5 to 72.5% by weight of the bio-acceptable polymer.

7. A method of claim 1, wherein the biopolymer sheet of the ligament and tendon repair device exhibits one or more of the characteristics selected from the group consisting of:
   (i) an average porosity of about 80 to 120 microns as determined by mercury porosimetry;
   (ii) an absorbance in vitro of about its own weight in blood in about 5 minutes and an absorbance of about twice its own weight in blood in about 20 minutes;
   (iii) substantial in vivo cell infiltration into the scaffold within about two weeks following implantation; and
   (iv) a 4 to 8-fold higher number of adhered cells after 2 to 8 weeks following subcutaneous implantation as compared to an implanted device comprised of Type I collagen and bio-acceptable polymers generated using an HFIP electroprocessing solvent.

8. A method of claim 1, wherein the DMSO solvent system comprises about 100% DMSO by weight.

9. A method of claim 2, wherein the DMSO solvent system comprises about 100% DMSO by weight.

10. A method of claim 6, wherein the DMSO solvent system comprises about 100% DMSO by weight.

11. A method of claim 1, wherein the bio-acceptable polymer is high viscosity PDLLA.

12. A method of claim 2, wherein the bio-acceptable polymer is high viscosity PDLLA.

13. A method of claim 6, wherein the bio-acceptable polymer is high viscosity PDLLA.

14. A method of claim 2, wherein the biopolymer fibers are collected to form a biopolymer sheet having a thickness that ranges from about 0.5 mm to about 6.0 mm.

15. A method of claim 2, wherein the biopolymer fibers are collected to form a biopolymer sheet having fibers laying in the transverse plane capable of providing biaxial support for suture retention.

16. A method of claim 2, wherein the biopolymer fibers are collected to form a biopolymer sheet having a first side having substantially aligned fibers and a second side having fibers that are not substantially aligned.

17. A method of claim 16, wherein the biopolymer fibers are collected to form a gradient of alignment from isotropic to anisotropic of the biopolymer fibers through the biopolymer sheet of about 25 to 33%.

18. A method of claim 17, wherein the gradient of alignment is in a layer or zone of the ligament and tendon repair device.

19. A method of claim 2, further comprising the step of marking the inner or outer surface of the implantable ligament and tendon repair device so as to distinguish the inner-facing from outer-facing sides of the device as implanted.

20. A method of claim 2, further comprising the step of packaging the implantable ligament and tendon repair device in a high barrier pouch.

21. A method of claim 2, wherein the biopolymer sheet of the ligament and tendon repair device exhibits one or more of the characteristics selected from the group consisting of:
(i) a range of tensile strength of about 4 to 16 MPa;
(ii) a modulus of elasticity of about 35-200 MPa; and
(iii) a peak stress 2.5 to 10 MPa.

22. A method of claim 1, wherein the biopolymer sheet of the ligament and tendon repair device exhibits one or more of the characteristics selected from the group consisting of:
(i) a range of tensile strength of about 4 to 16 MPa;
(ii) a modulus of elasticity of about 35-200 MPa; and
(iii) a peak stress 2.5 to 10 MPa.

23. A method of claim 1, wherein the biopolymer sheet of the ligament and tendon repair device exhibits a range of tensile strength of about 4 to 16 MPa.

24. A method of claim 1, wherein the biopolymer sheet of the ligament and tendon repair device exhibits a modulus of elasticity of about 35-200 MPa.

25. A method of claim 1, wherein the biopolymer sheet of the ligament and tendon repair device exhibits a peak stress 2.5 to 10 MPa.

26. A method of claim 5, wherein the biopolymer fibers are generated by electrospinning.

27. A method of claim 1, wherein the bio-acceptable polymer is PDLA.

28. A method of claim 1, wherein the bio-acceptable polymer is PDLLA.

29. A method of claim 1, wherein the bio-acceptable polymer is PLGA.

* * * * *